US008119365B2

(12) United States Patent
Blattner et al.

(10) Patent No.: US 8,119,365 B2

(45) **Date of Patent: *Feb. 21, 2012**

(54) INSERTION SEQUENCE-FREE BACTERIA

(75) Inventors: Frederick R. Blattner, Madison, WI (US); John W. Campbell, Oak Park, IL (US); David Frisch, Fitchburg, WI (US); Guy Plunkett, Madison, WI (US); Gyorgy Posfai, Szeged (HN)

(73) Assignee: Wisconsin Alumni Research Foundation, Madison, WI (US)

( * ) Notice: Subject to any disclaimer, the term of this patent is extended or adjusted under 35 U.S.C. 154(b) by 1546 days.

This patent is subject to a terminal disclaimer.

(21) Appl. No.: 11/400,711

(22) Filed: Apr. 7, 2006

(65) Prior Publication Data

US 2007/0054358 A1 Mar. 8, 2007

Related U.S. Application Data

(63) Continuation-in-part of application No. 11/275,094, filed on Dec. 9, 2005, and a continuation-in-part of application No. 10/896,739, filed on Jul. 22, 2004, now abandoned, which is a continuation of application No. PCT/US03/01800, filed on Jan. 22, 2003, which is a continuation-in-part of application No. 10/057,582, filed on Jan. 23, 2002, now Pat. No. 6,989,265.

(60) Provisional application No. 60/634,611, filed on Dec. 9, 2004, provisional application No. 60/409,089, filed on Sep. 6, 2002.

(51) Int. Cl.
*C12N 15/09* (2006.01)
*C12N 15/10* (2006.01)
*C12N 1/20* (2006.01)

(52) U.S. Cl. .................... 435/69.1; 435/91.1; 435/252.8

(58) Field of Classification Search ........................ None
See application file for complete search history.

(56) References Cited

U.S. PATENT DOCUMENTS

| | | | | |
|---|---|---|---|---|
| 4,851,348 | A | 7/1989 | Hanahan | 435/6 |
| 4,981,797 | A | 1/1991 | Jessee et al. | 435/252.8 |
| 5,578,464 | A | 11/1996 | Lunn et al. | 435/69.1 |
| 5,747,662 | A | 5/1998 | Simmons et al. | 536/24.1 |
| 5,824,502 | A | 10/1998 | Honjo et al. | 435/69.1 |
| 5,962,327 | A | 10/1999 | Dujon et al. | 435/478 |
| 6,015,709 | A | 1/2000 | Natesan | 435/366 |
| 6,022,952 | A | 2/2000 | Weiner et al. | 530/350 |
| 6,117,680 | A | 9/2000 | Natesan et al. | 435/455 |
| 6,238,924 | B1 | 5/2001 | Dujon et al. | 435/477 |
| 6,335,178 | B1 | 1/2002 | Weiner et al. | 435/69.1 |
| 6,372,476 | B1 | 4/2002 | Belguith et al. | 435/233 |
| 6,410,273 | B1 | 6/2002 | Crouzet et al. | 435/91.1 |
| 6,509,156 | B1 | 1/2003 | Stewart et al. | 435/6 |
| 6,989,265 | B2 | 1/2006 | Blattner et al. | 435/252.8 |
| 2003/0138937 | A1 | 7/2003 | Blattner et al. | 435/252.33 |
| 2005/0032225 | A1 | 2/2005 | Blattner et al. | 435/488 |

FOREIGN PATENT DOCUMENTS

| | | |
|---|---|---|
| EP | 0177343 | 4/1986 |
| EP | 0283726 | 9/1988 |
| WO | WO 88/05821 | 8/1988 |
| WO | WO 96/14408 | 5/1996 |
| WO | WO 01/27258 | 4/2001 |
| WO | WO 02/14495 | 2/2002 |
| WO | WO 03/048374 | 6/2003 |
| WO | WO 03/070880 | 8/2003 |
| WO | WO 2005/087940 | 9/2005 |

OTHER PUBLICATIONS

Khosla et al., "Expression of Recombinant Proteins in *Escherichia coli* Using an Oxygen-Responsive Promoter," *Bio/Technology*, 8:554-558, 1990.

Passoth et al., "Analysis of the hypoxia-induced ADH2 promoter of the respiratory yeast Pichia stipitis reveals a new mechanism for sensing of oxygen limitation in yeast," *Yeast*, 20:39-51, 2003.

Xu and Tabita, "Positive and negative regulation of sequences upstream of the form II cbb CO2 fixation operon of Rhodobacter sphaeroides," *J. Bacteriol.*, 176:7299-7308, 1994.

PCT/US2007/066087 International Search Report, mailed Sep. 17, 2007.

Posfai et al., "Emergent properties of reduced-genome *Escherichia coli," Science*, 312:1044-1046, 2002.

Sharma et al., "Recombinant protein production in an *Escherichia coli* reduced genome strain," *Metabolic Engineering*, 9:133-141, 2007.

Aristidou et al., "Modification of central metabolic pathway in *Escherichia coli* to reduce acetate accumulation by heterologous expression of the bacillus subtilis acetolactate synthase gene," *Biotechnology and Bioengineering*, 44:944-951, 1994.

Asai et al., "An *Escherichia coli* strain with all chromosomal rRNA operons inactivated: complete exchange of rRNA genes between bacteria," *Proc. Natl. Acad. Sci., USA*, 96:1971-1976, 1999.

Balbas, "Understanding the art of producing protein and non-protein molecules in *E. coli," Molec Biotechnol.*, 19:251-267, 2001.

Baneyx, "Recombinant protein expression in *E. coli," Curr Opin Biotech*, 10:411-421, 1999.

Bass et al., "Mulitcopy suppressors of Prc mutang *Escherichia coli* include two HtrA (DegP) protease homologs (HhoAB), DksA, and a truncated RlpA,"*Journal of Bacteriology*, 178(4):1154-1161, 1996.

Beaulieu et al , "Pathogenic behavior of pectinase-defective Erwinia chrysanthemi mutants on different plants," *MPMI*, 6(2):197-202, 1993.

Bermejo et al., "Expression of clostridium acetobutylicum ATCC 824 genes in *escherichia coli* for acetone production and acetate detoxification," *Applied and Environmental Microbiology*, 64:1079-1085, 1998.

Berry et al., "Application of metabolic engineering to improve both production and use of biotech indigo," *J Indust Micro & Biotech*, 22:127-133, 2002.

Blattner et al., "The complete genome sequence of *Escherichia coli* K-12," *Science*, 277:1453-1474, 1997.

(Continued)

*Primary Examiner* — Nancy Vogel

(74) *Attorney, Agent, or Firm* — Fulbright & Jaworski

(57) ABSTRACT

A bacteria lacking genomic and non-genomic IS elements is provided. The bacteria may be more stable and useful for the production of amino acids, polypeptides, nucleic acids and other products.

14 Claims, 8 Drawing Sheets

OTHER PUBLICATIONS

Blaudeck et al., "Specificity of single peptide recognition in TAT-dependent bacterial protein translocation," *J. Bacteriology*, 183:604-610, 2001.
Chang et al., "Acetate metabolism in a pta mutant of *Escherichia coli* W3110: Importance of maintaining acetyl coenzyme a flux for growth and survival," *Journal of Bacteriology*, 181:6656-6663, 1999.
Chou et al., "Effect of modified glucose uptake using genetic engineering techniques on high-level recombinant protein production in *Escherichia coli* dense cultures," *Biotechnology and Bioengineering* 44:953-960, 1994.
Contiero et al., "Effects of mutations in acetate metabolism on high-cell-density growth of *Eschrichia coli*," *Journal of Industrial Microbiology & Biotechnology*, 24:421-430, 2000.
Court et al., "Genetic engineering using homologous recombination," *Annu Rev Genet*, 36:361-388, 2002.
Danese et al., "Targeting and assembly of periplasmic and outer-membrane proteins in *Escherichia coli*," *Annu Rev Genet*, 32:59-64, 1998.
Database EMBL, "*E.coli* genomic DNA, Kohaia clone #421(55.1-55.5 min.)," Database Accession No. ECD874, 1999.
Datsenko and Wanner, "One-step inactivation of chromosomal genes in *Escherichia coli* K-12 using PCR products," *Proc. Natl. Acad. Sci. USA*, 97:6640-6645, 2000.
Dedhia et al., "Overproduction of glycogen in *Escherichia coli* blocked in the acetate pathway improved cell growth," *Biotechnology and Bioengineering*, 44:132-139, 1994.
Degryse, "Evaluation of *Escherichia coli* recBC sbcBC mutants for cloning by recombination in vivo," *J. Biotechnology*, 39:181-187, 1995.
DeLisa et al., "Quorum sensing via AI-2 communicates the metabolic burden associated with heterologous protein production in *E. coli*," *Biotech Bioeng*, 75(4):439-450, 2001.
Diaz-Ricci et al., "Effects of alteration of the acetic acid synthesis pathway on the fermentation pattern of *Escherichia coli*," *Biotechnology and Bioengineering*, 38:1318-1324, 1991.
Dykstra and Kushner, "Physical characterization of the cloned protease III gene from *Escherichia coli* K-12," *Journal of Bacteriology*, 163(3):1055-1059, 1985.
Eichhorn et al., "Deletion analysis of the *Escherichia coli* taurine and alkanesulfonate transport systems," *Journal of Bacteriology*, 182(10)2687-2695, 2000.
Farmer and Liao., "Reduction of aerobic acetate production by *Escherichia coli*," *Applied and Environmental Microbiology*, 63:3205-3210, 1997.
Fekkes and Driessen, "Protein targeting to the bacterial cytoplasmic membrane," *Microbiol. Mol. Biol. Rev.*, 63:161-193, 1999.
GenBank Accession No. AE014073, 2006.
GenBank Accession No. AE014075, 2006.
GenBank Accession No. AF348706, 2001.
GenBank Accession No. AP009048, 2006.
GenBank Accession No. U00096, 2006.
Gill et al., "A comparative study of global stress gene regulation in response to overexpression of recombinant proteins in *E. coli*," *Metabolic Engineering*, 2:178-189, 2000.
Hahm et al., "Characterization and evaluation of a pta (phoshotransacetylase) negative mutant of *Escherichia coli* HB101 as production host of foreign lipase," *Applied Microbiology and Biotechnology*, 42:100-107, 1994.
Hall, "Activation of the bgl operon by adaptive mutation," *Mol. Biol. Evol.*, 15:1-5, 1998.
Hanahan, "Studies on transformation of *Escherichia coli* with plasmids," *J. Mol. Biol.*, 166(4):557-580, 1983.
Hannig and Makrides, "Strategies for optimizing heterologous protein expression in *Escherichia coli*," *Trends Biotechnol.*, 16(2):54-60, 1998.
Hayashi et al., "Construction of a genetic linkage map of the model legume Lotus japonicus using an intraspecific F2 population," *DNA Research*, 8:11-22, 2001.
Hengen, "Better competent cells and DNA polymerase contaminants," *Trends in Biochem. Sci.*, 19:426-427, 1994.
Hengen, "Preparing ultra-competent *Escherichia coli*," *Trends in Biochem. Sci.*, 21:75-76, 1996.
Hockney, "Recent developments in heterologous protein production in *Escherichia coli*," *Trends Biotechnol.*, 12(11):456-632, 1994.
Holms, "Flux analysis and control of the central metabolic pathways in *Escherichia coli*," *FEMS Microbiology Reviews*, 19:85-116, 1996.
Holms, "The central metabolic pathways of *Escherichia coli*: relationship between flux and control at a branch point, efficiency of conversion to biomass, and excretion of acetate," *Current Topics in Cellular Regulation*, 28:69-105, 1986.
Hynds et al., "The sec-independent twin-arginine translocation system can transport both tightly folded and malfolded proteins across the thylakoid membrane," *J. Biol. Chem.*, 273:34868-34874, 1998.
Kakuda et al., "Construction of Pta-Ack pathway deletion mutants of *Escherichia coli* and characteristic growth profiles of the mutants in a rich medium," *Bioscience Biotechnology Biochemistry*, 58:2232-2235, 1994.
Kitamura et al., "DNA sequence changes in mutations in the ton B gene on the chromosome of *Escherichia coli* K-12: insertion elements dominate the spontaneous spectra,," *Jpn J. Genet*, 70:35-46, 1995.
Kolisnychenko et al., "Engineering a reduced *Escherichia coli* genome," *Genome Research*, 12:640-647, 2002.
Koob et al., "Minimizing the genome of *Escherichia coli*," *Ann NY Acad Science*, 745:1-3, 1994.
Koonin, "How many genes can make a cell: the minimal-gene-set concept," *Ann Rev Genome Hum Genet*, 1:99-116, 2000.
Lee, "High cell-density culture of *Escherichia coli*," *TIBECH*, 14:98-103, 1996.
Mersereau et al., "Efficient transformation of Agrobacterium tumefaciens by electroporation," *Gene*, 90:149-151, 1990.
Murphy, "Use of bacteriophage λ recombination functions to promote gene replacement in *Escherichia coli*," *J. Bacteriol.*, 180:2063-2071, 1998.
Muyrers et al., "Rapid modification of bacterial artificial chromosomes by ET-recombination," *Nucleic Acids Research*, 27:1555-1557, 1999.
Neidhardt et al., "Culture medium for Enterobacteria," *J. Bacteriol.*, 119:736-747, 1974.
Oliner et al., "In vivo cloning of PCR products in *E. coli*," *Nucleic Acids Research*, 2(22):5192-5197, 1993.
Otto and Silhavy, "Surface sensing and adhesion of *E. coli* controlled by the Cpx-signaling pathway," *Proc. Natl. Acad. Sci., USA*, 99(4):2287-2292, 2002.
Park et al., "MppA, a perplasmic binding protein essential for import of the bacterial cell wall peptide L-Ananyl-γ-D-glutamy-l-meso-diaminopimelate," *Journal of Bacteriology*, 180(5):1215-1223, 1998.
Perna et al, "Genome sequence of enterohemorrhagic *Escherichia coli* O157:H7," *Nature*, 409:529-533, 2001.
Perna et al., "The genomes of *Escherichia coli* K-12 and pathogenic *E. coli*," *Pathogenic E. coli Paradigm for Bacterial Pathogenesis*, M.S. Donnenberg, Editor, Academmic Press, 2002.
Pfeifer et al., "Biosynthesis of complex polyketides in metabolically engineered strain of *E. coli*," *Science* 291:1790-1792, 2001.
Ponce, "Effect of growth rate reduction and genetic modifications of acetate accumulation and biomass yields in *Escherichia coli*," *Biotechnology and Bioengineering*, 87:775-780, 1999.
Pope and Kent, "High efficiency 5 min transformation of *Escherichia coli*," *Nucleic Acids Research*, 24:536-537, 1996.
Posfai et al, "In vivo excision and amplification of large segments of the *Escherichia coli* genome," *Nucleic Acids Research*, 22(12):2392-2398, 1994.
Posfai et al., "Markerless gene replacement in *Escherichia coli* stimulated by a double-strand break in the chromosome," *Nucleic Acids Research*, 27:4409-4415, 1999.
Posfai et al., "Versatile insertion plasmids for targeted genome manipulations in bacteria: isolation, deletion, and rescue of the pathogenicity island LEE of the *Escherichia coli* O157:H7 genome," *J. Bacteriol.*, 179:4426-4428, 1997.
Pugsley, "The complete general secretory pathway in gram-negative bacteria," *Microbiol. Rev.*, 57:50-108, 1993.
Riesenberg, "High cell density cultivation of *E. coli* at controlled specific growth rate," *J. Biotech*, 20(10):17-27, 1991.

Riggs , "Expression and Purification of Maltose-Binding Protein Fusions," *Current Protocols Mol. Biol.*, 16.6.1-16.6.14, John Wiley and Sons, 1994.

Ritz and Beckwith, "Roles of thiol redox pathways in bacteria," *Annu Rev Microbiol*, 55:21-48, 2001.

Santini et al., "A novel sec-independent periplasmic protein translocation pathway in *Escherichia coli,*" *EMBO J.*, 17:101-112, 1998.

Sargent et al, "Overlapping functions of components of a bacterial sec-independent protein export pathway," *EMBO J*, 17:3640-3650, 1998.

Schaechter and Neidhardt., "Introduction," In: *Escherichia coli and Salmonella*, ed. Neidhart, FC et al., 1-2, ASM Press, Washington, D.C., 1997.

Schutz et al., "Sulfide-quinone reductase from Rhodobacter capsulatus: requirement for growth, periplasmic localization, and extension of gene sequence analysis," *Journal of Bacteriology*, 181(20):6516-6523, 1999.

Selinger et al., "RNA expression analysis using a 30 base pair resolution *Escherichia coli* genome array," *Nat Biotechnol*, 18(12):1262-1268, 2000.

Shiloach and Fass, "Growing *E. Coli* to high cell density-A historical perspective on method development," *Biotechnology Advances*, 23:345-357, 2005.

Shiloach et al. "Effect of glucose supply strategy on acetate accumulation, by *Escherichia coli* BL21 (lambda-DE3)and *Escherichia coli* JM109," *Biotechnology and Bioengineering*, 49:421-428, 1996.

Shuman, "Active transport of maltose in *Escherichia coli* K12," *J. Biol. Chem.*, 257(10):5455-5461, 1982.

Simmons and Yansura, "Translational level is a critical factor for secretion of heterologous proteins in *E. coli,*" *Nature*, 14:629-634, 1996.

Singh-Gasson et al., "Maskless fabrication of light-directed oligonucleotide microarrays using a digital micromirror array," *Nat Biotechnol.*, 17(10):974-978, 1999.

Smalley et al., "In search of the minimal *Escherichia coli* genome," *Trends in Microbiology*, 11(1):6-8, 2003.

Swartz, "Advances in *E. coli* production of therapeutic proteins," *Curr. Opin in Biotech*, 12:195-201, 2001.

Thomas et al., "Export of active green fluorescent protein to the periplasm by the twin-arginine translocase (TAT) pathway in *Escherichia coli,*" *Mol Micro*, 39(1):47-53, 2001.

Van Spanning et al., "Isolation and characterization of the moxJ, moxG, moxI, and moxR genes of Paracoccus denitrificans: Inactivation of moxJ, moxG, and moxR and the resultant effect on methylotrophic growth,"*Journal of Bacteriology*, 173(21):6948-6961, 1991.

Vellai et al., "Genome economization and a new approach to the species concept in bacteria," *Proc R Soc Lond B*, 266:1953-1958, 1999.

Venkatesan et al., "Complete DNA sequence and analysis of the large virulence plasmid of Shigella flexneir., "*Infection of Immunity*, 3271-3285, 2001.

Waller and Sauer, "Characterization of degQ and degS, *Escherichia coli* genes encoding homologs of the DegP protease," *Journal of Bacteriology*, 178(4):1146-1153, 1996.

Weiner et al., "A novel and ubiquitous system for membrane targeting and secretion of cofactor-containing proteins," *Cell*, 93:93-101, 1998.

Welch et al., "Extensive mosaic structure revealed by the complete genome sequence of uropathogenic *Escherichia coli,*" *Proc. Natl. Acad. Sci., USA*, 99(26):17020-17024, 2002.

Wirth et al., "Transformation of various species of gram-negative bacteria belonging to 11 different genera by electroporation," *Mol. Gen.Genet.*, 216:175-177, 1989.

Yang et al., "Metabolic flux analysis of *Escherichia coli* deficient in the acetate production pathway and expressing the bacillus subtilis acetolactate synthase," *Metabolic Engineering* 1:26-34, 1999.

Yu et al., "An efficient recombination system for chromosome engineering in *Escherichia coli,*" *Proc. Natl. Acad. Sci., USA*, 97:5978-5983, 2000.

Yu et al., "Minimization of the *Escherichia coli* genome using a Tn5-targeted Cre/LoxP excision system," *Nature Biotech*, 20:1018-1023, 2002.f.

Zhang et al., "A new logic for DNA engineering using recombination in *Escherichia coli,*" *Nature Genetics*, 20:123-128, 1998.

Zhang et al., "DNA cloning by homologous recombination in *Escherichia coli,*" *Nature Biotech.*, 18:1314-1317, 2000.

Zhang et al., "Phage annealing proteins promote oligonucleotide-directed mutagenesis in *Escherichia coli* and mouse ES cells," *BMC Molecular Biology*, 4:1, 2003.

INSERTION SEQUENCE-FREE BACTERIA

CROSS-REFERENCE TO RELATED APPLICATIONS

The present application is a continuation-in-part of U.S. application Ser. No. 11/275,094, filed Dec. 9, 2005, which in turn claims the benefit of U.S. Provisional Application No. 60/634,611, filed Dec. 9, 2004, and is a continuation-in-part of U.S. application Ser. No. 10/896,739 filed Jul. 22, 2004 (abandoned), which is a continuation of International Application No. PCT/US03/01800, filed Jan. 22, 2003, which claims the benefit of U.S. Provisional Application No. 60/409,089, filed Sep. 6, 2002 and which is a continuation-in-part of U.S. Application Ser. No. 10/057,582, filed Jan. 23, 2002, now U.S. Pat. No. 6,989,265.

FIELD OF THE INVENTION

The present invention relates to strains of microorganisms and processes involving these microorganisms. More specifically, the present invention relates to modified strains of microorganisms lacking all Insertion Sequence elements and the use thereof.

BACKGROUND OF THE INVENTION

Bacteria have been used to produce a wide range of commercial products. For example, many *Streptomyces* strains and *Bacillus* strains have been used to produce antibiotics; *Pseudomonas denitrificans* and many *Propionibacterium* strains have been used to produce vitamin B12; some other bacteria have been used to produce vitamins such as Riboflavin; *Brevibacterium flavum* and *Corynebacterium glutamicum* have been used to produce lysine and glutamic acid, respectively, as food additives; other bacteria have been used to produce other amino acids used as food additives; *Alcaligenes eutrophas* has been used to produce biodegradable microbial plastics; and many *Acetobacter* and *Gluconobacter* strains have been used to produce vinegar. More recently, bacteria, such as *Escherichia coli* (*E. coli*), have been genetically engineered and used as host cells for the production of biological reagents, such as proteins and nucleic acids, in laboratory as well as industrial settings. The pharmaceutical industry supports several examples of successful products, which are human proteins manufactured in *E. coli* cultures cultivated in a fermenter.

*E. coli* K-12 is the most commonly used host for cloning and other molecular biology techniques and is the platform of choice for production of metabolites such as amino acids and many proteins of therapeutic or commercial interest. Recently it has been used or proposed for production of therapeutic DNA for use in gene therapy, DNA vaccines, and RNA interference applications. The complete genomes of two closely related *E. coli* K-12 strains, MG1655 and W3110, have been sequenced and are available from the National Center for Biotechnology Information microbial genomes database (NCBI database) (www.ncbi.nih.gov/genomes/lproks.cgi) as accession numbers U00096 and AP009048 respectively. Eighty-seven percent of *E. coli* K-12 genes have been assigned functions with some degree of confidence, making it one of the best understood organisms.

Desirable properties for a platform microorganism include efficiency of production, purity of product and stability of the genome during experimental manipulation, in production, and in storage. The chromosome of *E. coli* is littered with mobile genetic elements that mediate horizontal gene transfer, including insertion sequences (IS), transposases, defective phages, integrases, and site-specific recombinases. These elements can translocate, duplicate, and be maintained in the genome like an infectious agent, and are known to hop into plasmids as well. IS elements may cause inversions, duplications, and deletions mediated by homologous recombination. This can happen even when the transposase function has become inactive. Similar rearrangements also result from rRNA and Rhs repeats, but the instability is magnified when active transposases are involved.

Genome alterations due to IS translocation occur surprisingly frequently, and many commonly used laboratory and industrial strains have unrecognized genome alterations from this cause. For example, many of the differences between the two sequenced *E. coli* K-12 strains, which have been separated for about five decades from a common laboratory ancestor, are due to IS hops. The sequence databases provide ample evidence that IS hopping into plasmids is also common on the time scale of laboratory manipulations. Approximately one in every thousand eukaryotic sequences in the public databases is inadvertently contaminated with bacterial IS elements that apparently hopped into the cloned eukaryotic DNA during the brief period of propagation in *E. coli* prior to sequencing.

IS elements can also be inadvertently introduced into strains by laboratory manipulations. A case in point involves the *E. coli* K-12 derivatives DH10B and DH5α, which carry an IS10 not present in the ancestral K-12 genome. Despite a report that residual IS10 elements do not exhibit transpositional mutagenesis in recA strains, such as DH10B and DH5α, the prominence of IS10 contamination of the eukaryotic databases shows that this continues to be an issue. Thus, IS elements may lead to unpredictable consequences with important production hosts and pose a considerable impediment to the efficiency and accuracy of amino acid, protein, and nucleic acid production in *E. coli.*

SUMMARY OF THE INVENTION

A non-naturally occurring bacterium is provided lacking genomic and non-genomic insertion sequences. The bacterium may be an *E. coli*. The genome of the bacterium may be less than 4.41 Mb, 4.27 Mb, 4.00 Mb, 3.71 Mb, 2.78 Mb or 1.86 Mb. The bacterium may be derived from strain *E. coli* K-12. The bacterium may also be derived from *E. coli* DH10B or *E. coli* DH5α. The bacterium may be competent to be transformed.

The bacterium may comprise an additional nucleic acid, which may lack insertion sequences. The additional nucleic acid may be a vector, which may be a plasmid. The additional nucleic acid may comprise another nucleic acid encoding a polypeptide. The polypeptide encoding nucleic acid may be operatively linked to an expression control sequence.

A method of propagating a nucleic acid is also provided. The nucleic acid may be toxic. A bacterium lacking genomic and non-genomic insertion sequences and an additional nucleic acid may be incubated under conditions allowing transformation of the bacterium with the nucleic acid which then may be grown under conditions allowing replication of the nucleic acid. Transformation may occur by electroporation. The nucleic acid may be amplified by propagating the bacterium, wherein the nucleic acid is amplified.

DETAILED DESCRIPTION

Figure 1:
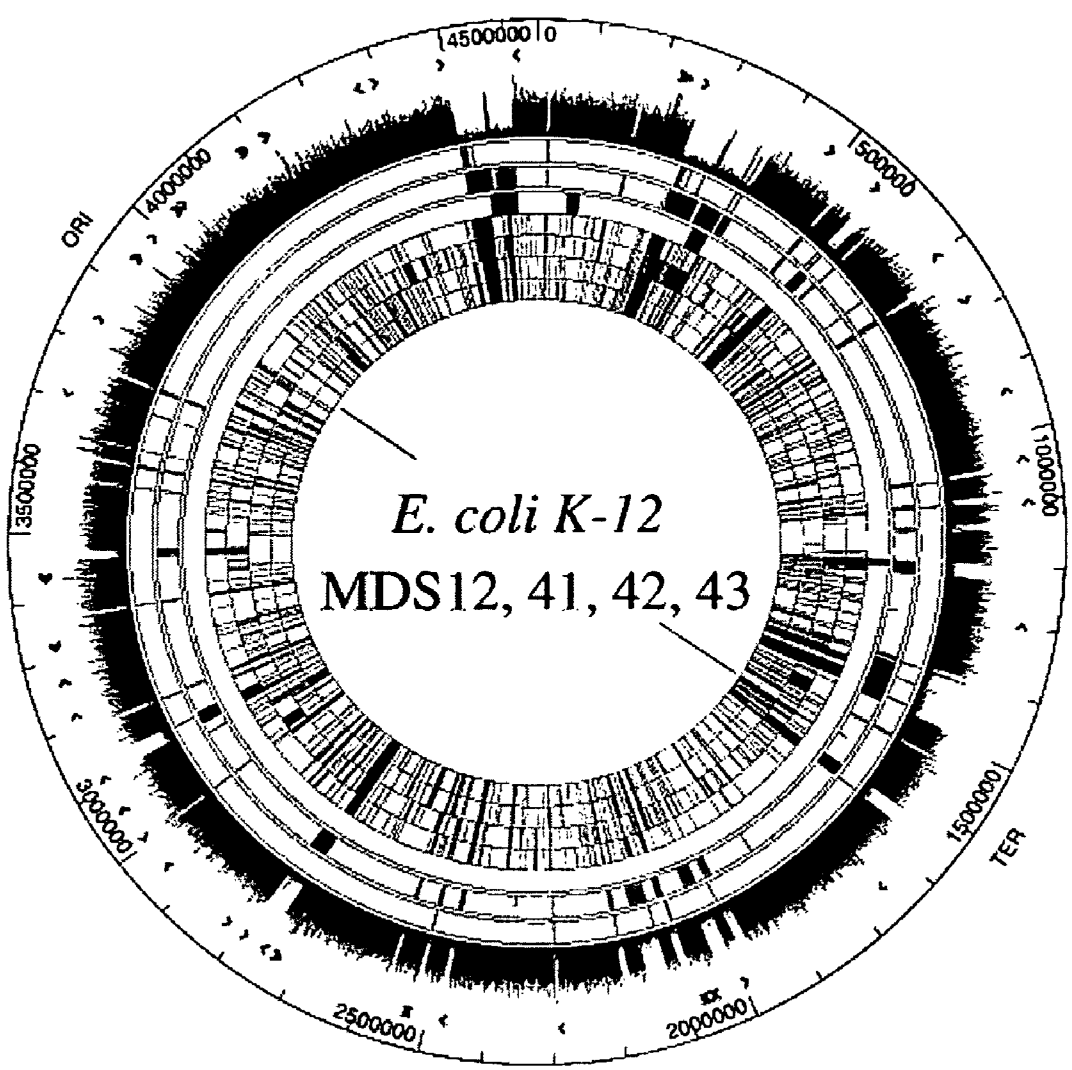
FIG. 1 is an illustration of the construction of an *E. coli* multiple deletion strain (MDS) lacking all IS elements. Concentric rings depict features mapped to the genome of the parental *E. coli* K-12 strain MG1655, numbered on the outer ring. Moving outward from the center, rings 1-5 (grey) show regions of K-12 that are absent in other sequenced *E. coli* genomes. Ring 6 shows the regions targeted for deletion. Ring 7 shows native IS and Rhs elements. Ring 8 shows experimental confirmation of the deletions in MDS43. The outer ring shows positions for the origin and terminus of replication and genes for rRNAs, tRNAs and other small stable RNAs.

The use of *E. coli* as a host organism for the production of biologically useful molecules has been plagued by genomic instability caused by mobile genetic elements such as IS elements. For example, IS elements can hop from host genomic nucleic acids into cloning vectors such as plasmids and thus are detrimental to the stability and efficiency of cloning. The role of extrachromosomal IS elements, such as IS mini-circles and other replicative and non-replicative IS derivatives is unappreciated and the presence of these in the host bacteria pose the same problem. A bacteria is provided lacking all genomic and non-genomic IS elements. The increased genetic stability of the bacteria is useful for such purposes as maintaining the integrity of cloned nucleic acids. The bacteria provides a more stable genetic environment for the production of nucleic acids, polypeptides, amino acids and other useful products.

1. Definitions

The terminology used herein is for the purpose of describing particular embodiments only and is not intended to be limiting. As used in the specification and the appended claims, the singular forms “a,” “an” and “the” include plural referents unless the context clearly dictates otherwise.

“Base pair” used herein may refer to the hydrogen bonded nucleotides of, for example, adenine (A) with thymine (T), or of cytosine (C) with guanine (G) in a double-stranded DNA molecule. In RNA, uracil (U) is substituted for thymine. Base pair may also be used as a unit of measure for DNA length.

“Clone” used in reference to an insert sequence and a vector may mean ligation of the insert sequence into the vector or its introduction by recombination either homologous, site specific or illegitimate as the case may be. When used in reference to an insert sequence, a vector, and a host cell, the term may mean to make copies of a given insert sequence. The term may also refer to a host cell carrying a cloned insert sequence, or to the cloned insert sequence itself.

“Complement,” “complementary” or “complementarity” used herein may mean Watson-Crick or Hoogsteen base pairing between nucleotides or nucleotide analogs of nucleic acid molecules. For example, the sequence 5'-A-G-T-3' is complementary to the sequence 3'-T-C-A-5'. Complementarity may be “partial”, in which only some of the nucleotides are matched according to the base pairing rules. Or, there may be “complete” or “total” complementarity between the nucleic acids. The degree of complementarity between nucleic acid strands may have effects on the efficiency and strength of hybridization between nucleic acid strands.

“Encoding” or “coding” used herein when referring to a nucleic acid may mean a sequence of nucleotides, which upon transcription into RNA and subsequent translation into protein, would lead to the synthesis of a given protein, peptide, or amino acid sequence. Such transcription and translation may actually occur in vitro or in vivo, or may be strictly theoretical based on the standard genetic code.

“Expression control sequence” used herein may mean a promoter or array of transcription factor binding sites that direct transcription of a nucleic acid operatively linked thereto.

“Nucleic acid” used herein may mean any nucleic acid containing molecule including, but not limited to, DNA or RNA. The term encompasses sequences that include any base analogs of DNA and RNA including, but not limited to, 4-acetylcytosine, 8-hydroxy-N-6-methyladenosine, aziridinylcytosine, pseudoisocytosine, 5-(carboxyhydroxylmethyl) uracil, 5-fluorouracil, 5-bromouracil, 5-carboxymethylaminomethyl-2-thiouracil, 5 carboxymethylaminomethyluracil, dihydrouracil, inosine, N6-isopentenyladenine, 1-methyladenine, 1-methylpseudouracil, 1-methylguanine, 1-methylinosine, 2,2-dimethylguanine, 2-methyladenine, 2-methylguanine, 3-methylcytosine, 5-methylcytosine, N6-methyladenine, 7-methylguanine, 5-methylaminomethyluracils, 5-methoxyaminomethyl-2-thiouracil, γ-D-mannosylqueosine, 5'-methoxycarbonylmethyluracil, 5-methoxyuracil, 2-methylthio-N6-isopentenyladenine, uracil-5-oxyacetic acid methylester, uracil-5-oxyacetic acid, oxybutoxosine, pseudouracil, queosine, 2-thiocytosine, 5-methyl-2-thiouracil, 2-thiouracil, 4-thiouracil, 5-methyluracil, N-uracil-5-oxyacetic acid methylester, uracil-5-oxyacetic acid, pseudouracil, queosine, 2-thiocytosine, and 2,6-diaminopurine.

“Operably linked” used herein may refer to an expression control sequence and downstream polynucleotide, such that productive transcription of the polynucleotide is initiated at the expression control sequence.

“Overexpressing” used herein may mean that the total cellular activity of protein encoded by a gene is increased. The total cellular activity of a protein may be due to increased cellular amounts of a protein, or increased half-life of the protein. Total cellular amounts of a protein may be increased by methods including, but not limited to, amplification of the gene coding said protein, operatively linking a strong promoter to the gene coding said protein or by increasing the strength of the genes' native promoter by, for example, mutating the promoter.

"Plasmid" used herein may mean extrachromosomal genetic elements composed of DNA or RNA that are not part of a chromosome but can propagate themselves autonomously in cells. A plasmid may refer to not only those native plasmids isolated from cells, but also any modified or chimeric versions (e.g., having deletions, additions or substitutions or assembled from functional parts of different plasmids) so long as they retain the ability to propagate themselves autonomously in cells.

"Phage" used herein may mean extrachromosomal bacteriophage capable of propagating in cells, such as bacteriophage P1, and also includes lysogenic bacteriophage such as Lambda that can integrate into, and propagate within, the host chromosome. A phage may refer to not only naturally occurring bacteriophage, but also any modified or chimeric versions (e.g. having deletions, additions or substitutions or assembled from functional parts of different phage) so long as they retain the ability to propagate in cells either autonomously or with helper function provided, for example, by helper phage.

"Protein" used herein may mean a peptide, polypeptide and protein, whether native or recombinant, as well as fragments, derivatives, homologs, variants and fusions thereof.

"Region of comparison" used herein when referring to a genome may be $1\times10^7$, $1.5\times10^7$, $2\times10^7$, $2.5\times10^7$, $3.5\times10^7$, $4\times10^7$ or more nucleotides or base pairs, and when referring to a nucleic acid sequence may be 50, 100, 250, 500, $10^3$, $5\times10^3$, $10^4$, $5\times10^4$, $10^5$, $5\times10^5$, $10^6$ or more nucleotides or more base pairs.

"Substantially complementary" used herein may mean that a first sequence is at least 60%, 65%, 70%, 75%, 80%, 85%, 90%, 95%, 97%, 98%, or 99% identical to the complement of a second sequence over a region of comparison or that the two sequences hybridize under stringent hybridization conditions.

"Substantially identical" used herein may mean that a first and second sequence are at least 60%, 65%, 70%, 75%, 80%, 85%, 90%, 95%, 97%, 98%, or 99% identical or substantially complementary over a region of comparison. A reference sequence and a test sequence may be aligned, manually or by a computer algorithm (e.g., GAP, BESTFIT, FASTA and TFAST), and the percentage identity calculated by dividing "the total number of identical residues" by "the total number of residues in the reference sequence" and then multiplying by 100.

"Vector" as used herein may mean a carrier DNA molecule into which a nucleic acid sequence can be inserted for introduction into a new host cell where it may be replicated, and in some cases expressed. Vectors can be derived from plasmids, bacteriophages, plants, animals viruses, etc. The vector may be propagated in the host cell as an extrachromomal element or, alternatively, the vector may integrate into the host cell genome and produce additional copies of the nucleic acid molecules when the host cell replicates.

2. Bacteria Lacking Insertion Sequences

A non-naturally occurring bacteria is provided lacking genomic and non-genomic IS elements. IS elements and their associated transposases are often found in bacteria and are associated with instabilities that can interfere with standard industrial or laboratory practices and might entail costly and burdensome quality control procedures. IS elements may be contained not only in genomic host nucleic acids, but also in non-genomic host nucleic acids.

An IS element may be linear or circular. For example, the IS element may be circularized to form an IS-mini circle. Creation of IS mini-circles may be the first step in the transposition process of an IS element. For example, creation of an IS-mini-circle is the first step in the transposition process of IS elements belonging to the IS2 family. IS elements are common in *E. coli* and all of them may be deleted.

IS elements are currently grouped into families based on conserved motifs. IS families include, without limitation, IS, IS3, IS4, IS5, IS6, IS2J, IS30, IS66, IS91, IS110, IS200/605, IS256, IS481, IS630, IS982, IS1380, ISAs1, ISL3, Tn3, and variants thereof. A variant may contain any of the conserved regions that define any of the IS families. Representative conserved regions include, but are not limited to the DDE motif, conserved in most IS element families, and the N-terminal helix-turn-helix motif, conserved in members of the IS3 family. The ISFinder database (www-is.biotoul.fr) contains the sequences of various members of the IS families. Each member of each IS family may be deleted.

a. Parent

The parent of the ISfree bacteria may be any bacterial strain that contains IS elements, as well as an intermediate strain from which the bacterium is derived. Representative examples of parent strains include, but are not limited to, *E. coli* strains such as K-12 or B, or a strain with a genome sequence substantially identical thereto. The *E. coli* K-12 strain may be a derivative strain including, but not limited to MG1655, DH10B, DH5α, Invα, Top10, Top10F, JM103, JM105, JM109, MC1061, MC4100, XL1-Blue, EC100 or EC300. The nucleotide sequence of the genome of the parental strain may be partially or completely known. The complete genomic sequence of several strains of *E. coli* and other commonly used laboratory microorganisms is known (see, e.g., Blattner et al., *Science,* 277:1453-74, 1997; GenBank Accession No. U0096; NCBI database, Accession No. AP009048, Perna et al., *Nature,* 409, 529-533, 2001; Hayashi et al., *DNA Res.,* 8, 11-22, 2001; Welch et al., *Proc. Natl. Acad. Sci., USA* 99:17020-17024, 2002 and GenBank Accession No. AE014075, each of which is incorporated herein by reference). The genomic sequence of DH10B is partially known (www.hgsc.bcm.tmc.edu/projects/microbial/EcoliDH10B).

*E. coli* strains MG1655 and W3110 have been sequenced and each contains a variety of IS elements, including: IS1, a member of the IS1 family; IS2, IS3 and IS150, members of the IS3 family; IS4 and IS 186, members of the IS4 family; IS5, a member of the IS5 family; and IS30, a member of the IS30 family. Additionally, partial sequences of IS600 and IS911, members of the IS3 family, are found in each strain. Frequency of occurrences of IS elements are presented in Table 1. Because DH10B is an *E. coli* K12 derivative, it is expected to have a similar IS composition to MG1655 and W3110.

TABLE 1

Frequency of IS elements in select *E. coli* K-12 strains

| IS element | MG1655 | W3110 | DH10B |
|---|---|---|---|
| IS1 | 7 | 8 | present |
| IS2 | 6 | 10 | present |
| IS3 | 5 | 5 | present |
| IS4 | 1 | 1 | present |
| IS5 | 11 | 18 | present |
| IS30 | 3 | 3 | present |
| IS150 | 1 | 1 | present |
| IS186 | 3 | 3 | present |

TABLE 1-continued

| Frequency of IS elements in select *E. coli* K-12 strains | | | |
|---|---|---|---|
| IS element | MG1655 | W3110 | DH10B |
| IS600 | partial | partial | ? |
| IS911 | partial | partial | ? |
| IS10 | 0 | 0 | present |

The nucleic acid sequence of *E. coli* MG 155 (annotated version m56), (NCBI accession no. U00096.1) is set forth in SEQ ID NO: 1 with a total size of 4,639,675 nucleotides or base pairs. The original release of the genomic sequence of *E. coli* MG1655 was annotated version m54, (NCBI accession no. U00096.1) (4,639,221 nucleotides or base pairs). Positions of the IS elements on a genome map of *E. coli* MG1655 (annotated version m54) are shown in FIG. 1 and Table 2 of U.S. Patent Publication No. 20030138937 and International Patent Publication No. WO 2003/070880, the contents of which are incorporated herein by reference.

b. Genomic Deletions

The bacteria may be made by deleting IS elements using any of the several methods known to those of skill in the art for deleting genomic or non-genomic nucleic acid. The nucleic acid sequences may be deleted from genomic or from non-genomic genetic material.

Representative methods for making deletions in the genome of a bacterium are described in U.S. Patent Publication No. 20030138937 and International Patent Publication No. WO 2003/070880, Posfai, G. et al., *J. Bacteriol.* 179: 4426-4428 (1997), Muyrers, J. P. P. et al., *Nucl. Acids Res.* 27:1555-1557 (1999), Datsenko K. A. et al., *Proc. Natl. Acad. Sci.* 97:6640-6649 (2000) and Posfai, G. et al., *Nucl. Acids. Res.* 27: 4409-4415 (1999), each of which is incorporated herein by reference. The deletion methods may be classified to those that are based on linear DNA and those that are based on suicide plasmids. The methods disclosed in Muyrers, J. P. P. et al., *Nucl. Acids Res.* 27:1555-1557 (1999) and Datsenko, K. A., *Proc. Natl. Acad. Sci.* 97:6640-6649 (2000) are linear DNA-based methods and the methods disclosed in n Posfai, G. et al., *J. Bacteriol.* 179: 4426-4428 (1997) and Posfai, G. et al., *Nucl. Acids Res.* 27: 4409-4415 (1999) are suicide plasmid-based methods.

In addition to IS elements, additional nucleic acids regions may be deleted from the bacteria. For example, in addition to IS elements, the bacteria may also be lacking one or more of the nucleic acid regions set forth on Table 2, or sequences substantially similar thereto, and those set out in Table 1 of U.S. Provisional Application No. 60/709,960, incorporated herein by reference. The bacteria may be strain MDS39, MDS41, MDS42, MDS43, or a strain with a genome substantially identical thereto. FIG. 1 is a map of MDS41, MDS42, and MDS43, all of which lack IS elements. The bacteria may also be MDS42recA or a strain with a genome substantially identical thereto. The bacteria may have a genome that is less than 4.41 Mb, 4.27 Mb, 4.00 Mb, 3.71 Mb, 2.78 Mb, or 1.86 Mb. Elimination of unnecessary genes may improve metabolic efficiency and perhaps simplify the purification of desirable products.

c. Competent Bacteria

The bacteria may be competent for transformation by a foreign molecule, such as a nucleic acid. The bacteria may be made competent by methods well known in the art. Representative methods of making the bacteria competent may be found in U.S. Pat. No. 4,981,797 and U.S. Patent Publication No. 20050032225, which are hereby incorporated by reference.

Removal of IS elements may lead to increased electroporation efficiency. For example, electroporation efficiency of strains MDS41, MDS42, and MDS43, from which all genomic IS elements are deleted, is improved by 2 orders of magnitude over their MG1655 parent and is comparable to DH10B, normally considered to be the best *E. coli* for electroporation.

d. Bacteria Comprising a First Nucleic Acid

The bacteria may comprise an additional nucleic acid, which may lack IS elements. The additional nucleic acid may be a vector, which may, inter alia be a plasmid, cosmid, BAC, modified YAC, phagemid or phage. The vector may be a cloning vector or an expression vector.

The additional nucleic acid may comprise another nucleic acid encoding a polypeptide. The polypeptide may be a therapeutic product including, but not limited to, a vaccine component, a diagnostic product, or a research reagent. Further, the polypeptide may be a protein, including but not limited to, insulin, an interleukin, a cytokine, a growth hormone, a growth factor, erythropoietin, a colony stimulating factor, interferon, an antibody and an antibody fragment. Expression of the polypeptide may be under the control of an inducible promoter or a promoter that is constitutively expressed in the bacteria. For example, lac-based promoter/repressor, inducible by the non-metabolisable galactose derivative, IPTG, may be used.

A first nucleic acid lacking IS elements may be useful for cloning. For example, overexpressing even a well tolerated protein-of-interest may lead to elevated IS transposition rates. Such transposition may result in the insertion of an IS element into the nucleic acid encoding the protein-of-interest.

3. Methods a. Cloning

The bacteria may be used to clone a nucleic acid. Briefly, the competent bacteria may be incubated with a nucleic acid under conditions allowing transformation of the bacteria by the nucleic acid. Conditions allowing transformation are well known in the art and may include, but are not limited to, electroporation, calcium or manganese chloride precipitation, lipofection, microinjection and natural transformation.

By providing a bacteria lacking genomic and non-genomic IS elements, cloning artifacts caused by transposable IS elements may be eliminated. Toxic nucleic acids may therefore be cloned in the bacteria. A "toxic" nucleic acid may be a nucleic acid which, when propagated in a host strain, results in an elevated rate of IS element transposition. Toxic nucleic acids are difficult to clone in bacterial hosts containing IS elements. For example, a nucleic acid encoding the open reading frame of VP60 of rabbit haemorrhagic disease virus fused to the B subunit of cholera toxin, previously incapable of being cloned due to the high rate of IS element transposition, has been successfully cloned in IS-free bacteria. In another example, pT-ITR, a plasmid possessing a stem-loop structure that prevents propagation in bacterial hosts containing IS elements, has been successfully propagated in IS-free bacteria.

Because IS element transposition may result in detectable insertion mutations, an elevated rate of IS element transposition of a toxic nucleic acid may be determined by comparison to the mutation rate of a host strain propagating a control nucleic acid. The insertion mutation rate of a host strain propagating the nucleic acid may be measured by the appearance of mutant cells that gain the ability to utilize salicin as a carbon source. Metabolism of salicin in *E. coli* K-12 requires activation of the bgl operon, which occurs primarily by integration of an IS element into the promoter region, as described in Hall, *Mol. Biol. Evol.,* 15:1-5, 1998, which is incorporated herein by reference. The toxic nucleic acid may encode a polypeptide, in which case the rate of IS element transposition may be compared to that resulting from the propagation, in the same host strain, of a control nucleic acid of similar size encoding a different polypeptide. The toxic nucleic acid may also be a vector, in which case the rate of IS element transposition may be compared to that resulting from the propagation, in the same host strain, of a different vector of similar size. Representative vectors include, but are not limited to pBR322, pUC18, pGEM, and pBluescript.

b. Expression

The bacteria may also be used for the production of polypeptides. Briefly, a bacteria comprising an additional nucleic acid which comprises a nucleic acid encoding a polypeptide, as described above, may be incubated under conditions allowing expression of the polypeptide product.

Overexpression of even a well tolerated protein-of-interest may lead to elevated IS transposition rates. Such transposition may result in the insertion of an IS element into the nucleic acid encoding the protein-of-interest. A bacteria comprising a nucleic acid encoding a polypeptide and lacking genomic and non-genomic IS elements may provide an increased production of protein.

Recombinant proteins may be expressed in the periplasm or cytoplasm. The expression of proteins in the periplasm is routinely used for industrial use and has been reviewed in Hanahan, *J. Mol. Biol.,* 166:557-80, 1983; Hockney, *Trends Biotechnol.,* 12:456-632, 1994; and Hannig et al., *Trends Biotechnol.,* 16:54-60, 1998, each of which is incorporated herein by reference. Recombinant proteins may be produced in the periplasm by expressing fusion proteins in which they are attached to a signal peptide that causes secretion into the periplasmic space. There the signal peptide may be cleaved off by specific signal peptidases. The protein transported into the periplasmic space may be biologically active.

The recombinant protein may also be co-expressed with chaperones/disulfide-bond forming enzymes, which may provide proper folding of the recombinant protein. Nucleic acid sequences of such proteins useful for periplasmic expression of recombinant protein include, but are not limited to, those described in U.S. Pat. Nos. 5,747,662; 5,578,464; 6,335,178; and 6,022,952; Thomas et al., *Mol-Micro*, (2001) 39 (1) 47-53; Weiner et al., *Cell*, (1998) 93, 93-101; and Current Protocols in Molecular Biology (1994) 16.6.1-16.6.14 (Copyrighted 2000 by John Wiley et al. and Sons), each of which is incorporated herein by reference.

c. Amplification

The reduced genome strain may also be used to amplify a nucleic acid. Briefly, a bacteria comprising a first nucleic acid lacking IS elements, may be incubated under conditions allowing the propagation of the first nucleic acid lacking IS elements.

The present invention has multiple aspects, illustrated by the following non-limiting examples.

EXAMPLE 1

Production of MDS39

Reduced genome strain MDS39 was produced as described in International Patent Publication No. WO 2003/070880, which is incorporated herein by reference. Briefly, a series of reduced genome strains (MDS01-MDS39) were produced by constructing a series of cumulative deletions of nucleic acid sequences from the parental strain *E. coli* MG1655 (annotated version m56)(SEQ ID NO: 1).

EXAMPLE 2

Production of MDS40-MDS43

Hybridization to genome scanning chips (NimbleGen Systems, Madison, Wis.) containing the K-12 sequence and all sequences in the IS database revealed that MDS39, the first strain designed to lack all IS elements, unexpectedly contained additional copies of IS elements that had hopped to new locations during its production. These IS elements were deleted to produce MDS40. The fhuACDB (the tonA locus) was deleted from MDS40 to produce MDS41. Strains lacking the tonA locus are resistant to infection by bacteriophage T1, a common laboratory scourge. The endA gene was deleted from MDS41 to produce MDS42. Loss of the endA-encoded endonuclease facilitates plasmid preparation. MDS43 was produced by deleting an additional 45 kb covering the lac operon from parental strain MDS42. The resulting MDS strains were again characterized by DNA chip hybridization. As shown in FIG. 1, for MDS43 (and for MDS41 and 42; data not shown) there is no evidence for any contaminating IS elements. Rings depict features mapped to the genome of the parental *E. coli* K-12 strain MG1655, numbered on the outer ring. Moving outward from the center, rings 1-5 (grey) show regions of K-12 that are absent in other sequenced *E. coli* genomes: RS218, CFT073, *S. flexneri* 2457T, EDL933 and DH10B. Ring 6 shows the regions targeted for deletion: MDS12 (red), MDS41 (yellow), MDS42 (blue), and MDS43 (purple); half-height black bars indicate 4 rogue IS elements detected and cleanly removed during strain construction. Ring 7: native IS (green) and Rhs elements (light blue). Ring 8: experimental confirmation of the deletions in MDS43 by a NimbleGen tiling chip; probes corresponding to the intended deletions are colored green, other probes are colored red. On the outer ring the positions of the origin and terminus of replication and genes for rRNAs (blue), tRNAs (turquoise) and other small stable RNAs (black) are indicated. The genome characteristics of new MDS strains MDS41-43 are summarized in the Table 3:

TABLE 3

Genome statistics of MG1655 and related multiple deletion strains

| | MG1655 | MDS12 | MDS41 | MDS42 | MDS43 |
|---|---|---|---|---|---|
| total no. genes | 4444 | 4029 | 3743 | 3742 | 3704 |
| genome size (bp) | 4639675 | 4263492 | 3977067 | 3976359 | 3931408 |
| replichore imbalance (bp) | 30517 | 141360 | 139331 | 138623 | 183574 |
| total no. genes deleted | 0 | 415 | 701 | 702 | 740 |
| total bp DNA deleted | 0 | 376183 | 662608 | 663316 | 708267 |
| % genome deleted | 0 | 8.11% | 14.28% | 14.30% | 15.27% |
| total no. ISs deleted | 0 | 22 | 42 | 42 | 42 |

EXAMPLE 3

Detection of IS Contamination of Plasmid Preparations

Figure 2:
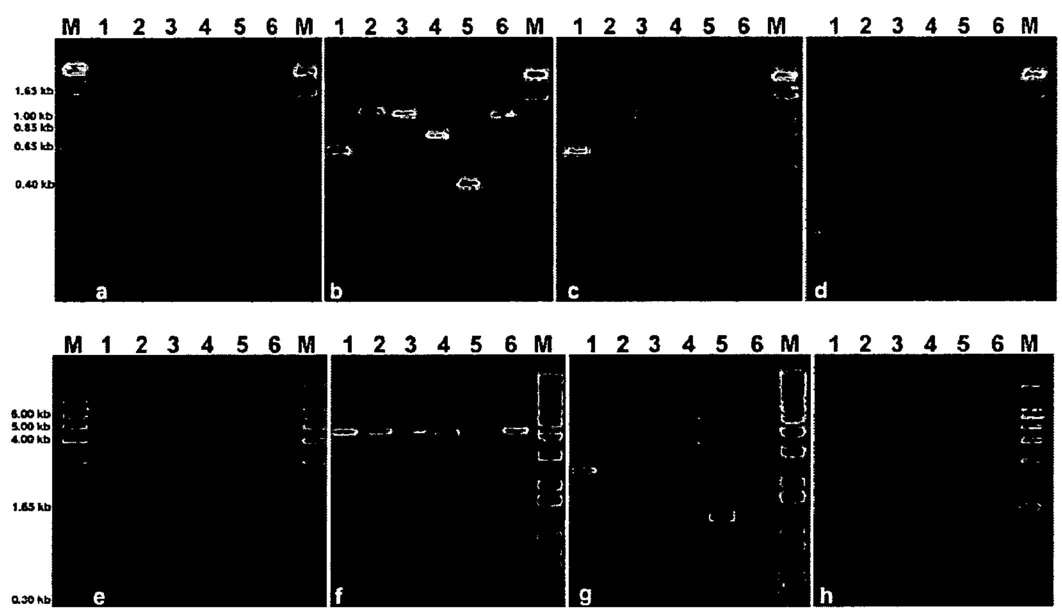
FIG. 2 shows the PCR detection of IS elements in various DNA preparations. Each panel is loaded in the same order: 1 kb+ marker, IS1, IS2, IS3, IS5, IS10, IS186, 1 kb+ marker, for (1) Positive Control, (2) Negative Control, (3) pBR322 from Invitrogen (in DH10B), and (4) pBR322 produced in MDS42.

A commercial preparation of pBR322 plasmid DNA, grown on DH10B according to the manufacturer, was compared to MDS grown plasmid. PCR amplification was done with inward and outward primers specific for IS1, IS2, IS3, IS5, IS10 and IS186 (FIG. 2, lanes 1-6 respectively; M is 1 kb+size standard). Outward primers (FIG. 2, panels e-h) detect circular structures, whereas inward primers (FIG. 2, panels a-d) detect both linear and circular IS forms. Positive controls were constructed by cloning each IS type (minus about 20 base pairs from its ends to prevent mobilization) into pBR322 (FIG. 2, panels b and f). FIG. 2, panels a and e are negative controls containing no DNA. Both sets of primers detected IS elements in the DH10B-grown prep (FIG. 2, panels c and g). The circular forms include some with sizes expected for a simple insertion of the IS into the plasmid, while others are consistent with a circle the size of the element itself. Cloning and sequencing further characterized products of the outward primer reactions. IS1, IS2, IS5 and IS10 gave examples of simple insertions at various positions in the plasmid. To detect mini-circle forms of IS elements, outward primed PCR reactions were directly sequenced with one of the primers. IS2 gave sequence results consistent with the presence of mini-circles. Plasmids grown in MDS42, on the other hand, contained no contaminating IS elements (FIG. 2, panels d and h). This indicates that removal of IS elements from host nucleic acids eliminates the hopping of IS elements from host nucleic acids to plasmid nucleic acids during cloning.

EXAMPLE 4

Figure 3:
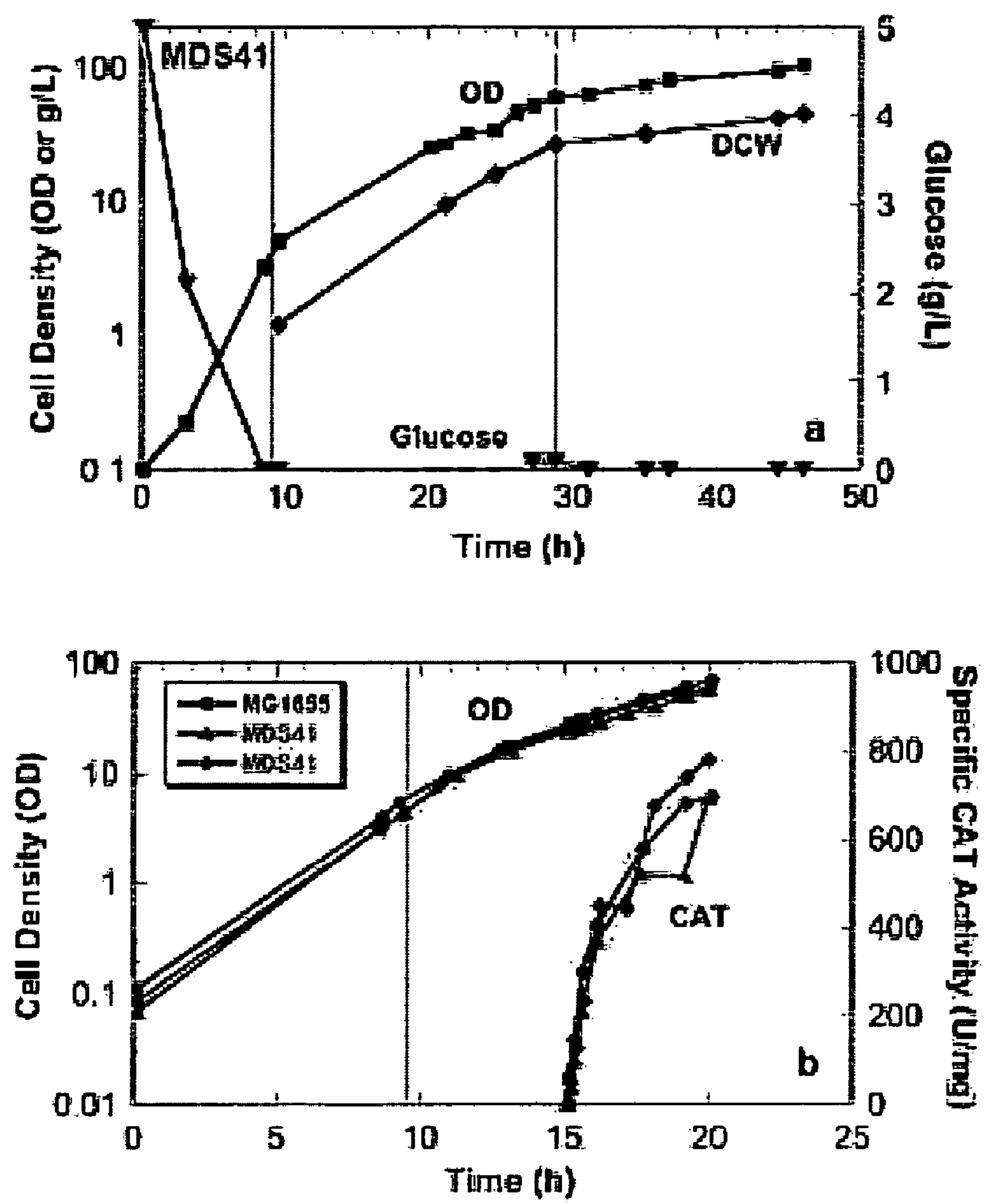
FIGS. 3*a* and 3*b* show the growth rate of strains MDS41, MDS42 and MDS43 in MOPS minimal medium at 37° C. (top) and a comparison of the growth rates and CAT expression of MG1655 and MDS42 in MOPS minimal medium at 37° C. (bottom).

Growth Rate of and Recombinant Protein Production in Strains Lacking IS Elements Strains MDS41, MDS42 and MDS43 were characterized for growth in standard microbiological media. FIG. 3(*a*) shows that each of the MDS strains can be grown to high cell densities in fed-batch fermentations on minimal medium. MDS41 was cultured in a minimal medium. Three growth phases were used to reach a dry cell weight (DCW) of 44 g/l. The first phase was a simple batch process. The second phase was a fed-batch process where the growth rate was controlled to 0.15 $h^{-1}$. The third growth phase (also a fed-batch process) had a significantly lower controlled growth rate to prevent exceeding the oxygen transfer rate of the fermenter. For the targeted cell density, a controlled growth rate of 0.03 $h^{-1}$ was used. FIG. 3(*b*) shows that the growth rate of MDS42 was essentially unchanged relative to the parental strain MG1655 in MOPS minimal medium at 37° C. Doubling time was obtained by measuring OD600 of cultures grown in baffled flasks at 37° C. The log linear portion of the growth curve was used to calculate the average doubling times and standard deviation from six replicates on the plate. The doubling time of MG1655 was 61.3 minutes compared to a doubling time of 69.07 minutes for MDS42. FIG. 3(*b*) shows that expression of recombinant proteins was similar for the MDS and MG1655 strains based on expression of the model protein chloramphenicol acetyl transferase (CAT).

EXAMPLE 5

Transformation Efficiency of Strains Lacking IS Elements

Strain MDS42 was compared to MG1655 and DH10B for transformation efficiency. Cells were grown under standard growth conditions to an optical density of 2.0 at 600 nm. Electrocompetent cells were prepared according to the method of Dower et al., Nucleic Acids Res (1988) 16, 6127-6145, incorporated herein by reference, and stored as frozen aliquots in 15% glycerol at a final optical density of 200 at 600 nm. Electroporation in an Eppendorf model 2510 instrument was at 18 kv/cm using 0.1 pg pUC 19 or 50 pg pCC145 DNA added to 0.1 ml of competent cells. The median of five electroporations is presented, each with a different batch of competent cells. For commercial competent cells of DH10B the five determinations were from different tubes of the same batch. With 20 kV/cm as recommended by their manufacturer, the commercial cells gave slightly higher values of $82.3\times10^8$ for pUC19 and $6.1\times10^6$ for pCC145 DNA. A t-test (p=0.002) indicates the transformation efficiency of MDS42 is significantly improved over MG1655 for electroporation with both large and small plasmid DNAs. As shown in Table 4, MDS42 has a substantially higher transformation efficiency compared to MG1655. Commercial competent cells are indicated by *:

TABLE 4

| Electroporation Efficiency (transformants/μg DNA) | | |
|---|---|---|
| Strain | pUC19 (2.686 kb) | pCC145 (pCC1BAC ™-145; Epicentre) (153 kb) |
| MG1655 | $0.7 \times 10^8$ | 0 |
| DH10B | $35.0 \times 10^8$ | $1.9 \times 10^6$ |
| DH10B* | $35.4 \times 10^8$ | $6.5 \times 10^6$ |
| MDS42 | $130.0 \times 10^8$ | $10.0 \times 10^6$ |

EXAMPLE 6

DNA Stability in Strains Lacking IS elements

Figure 4:
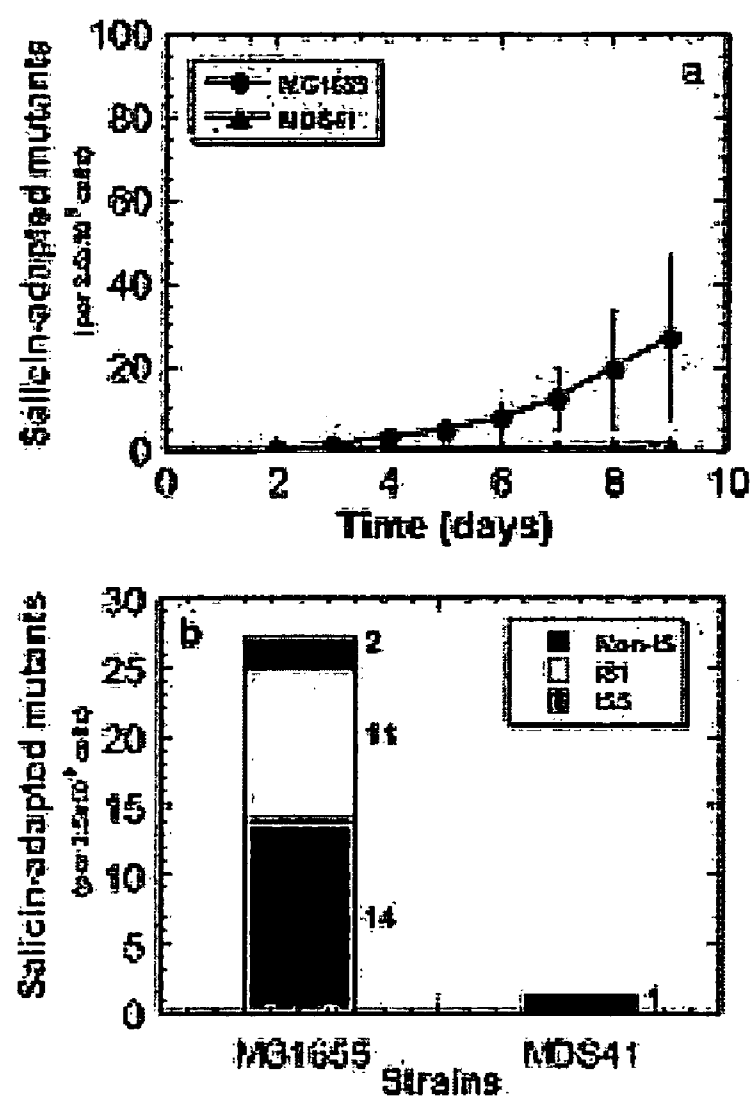
FIG. 4 compares the frequency of mutation by IS hopping to the genome in MDS41 and MG1655 as measured by the acquired ability to utilize salicin as a carbon source.

FIG. 4(*a*) shows that the measured frequency of mutation by IS hopping dropped to zero in strains lacking IS elements. Briefly, populations of MDS41 and parental MG1655 were monitored for appearance of mutant cells that gained the ability to utilize salicin as a carbon source. Metabolism of salicin in *E. coli* K-12 requires activation of the bgl operon, which occurs primarily by integration of an IS element into the promoter region. Cell populations were grown to saturation in glucose/minimal medium, then spread on minimal plates containing salicin as the sole carbon source. New colonies (adaptive mutants) were marked and counted each day for 9 days. The data shown in FIG. 4(*a*) are the mean from three independent experiments. Total plated cell numbers were calculated by plating appropriate dilutions from 2-5 parallel cultures onto rich medium. The mean colony numbers were normalized to $2.5\times10^9$ cells. A two-factor ANOVA analysis ($\alpha \leqq 0.05$) with post-hoc (t-tests) was used to determine if the adaptation rates (the mutant number/day) were significant with respect to strain or time. Both the time and strain/plasmid were determined to be significant ($p \leqq 0.001$). The interaction of time and strain/plasmid was determined not to be significant. Relative to MG1655, MDS41 displayed a >92% decrease in the rate of activation of the bgl operon. PCR analysis of the adaptive mutants indicates the decrease is due to the complete absence of IS-generated mutations in MDS41. FIG. 4(*b*) shows the spectrum of mutations in the bglR region of MG1655 and MDS41 cells adapted to salicin/minimal medium on day 9.

EXAMPLE 7

Stability of BAC libraries in Strains Lacking IS elements

Many large-scale sequencing projects of medical and commercial importance rely on large insert libraries commonly referred to as Bacterial Artificial Chromosomes (BACs). These recombinant constructs are composed of very large contiguous sequences of the subject DNA, on the order of 100 kb or larger, in combination with a selectable marker and a stable, low-copy number origin of replication to allow the molecule to replicate in a bacterial host. These molecules represent large targets for IS element insertion and are frequently subject to IS-mediated rearrangements, including deletions and inversions, which are difficult to detect by electronic bioinformatics methods. Minimizing bacterial DNA contamination (via IS element movement) represents an enormous improvement in the utility of BAC strategies for sequencing genomes. IS free strains of *E. coli* allow a precise measurement of the extent to which IS elements contaminate BAC DNA libraries.

A human BAC library created and maintained in *E. coli* DH10B was used to test the extent of IS element incorporation in BAC DNA. Forty-five random clones were picked from the 32,000 clone tiled human library collection and grown overnight in 1 ml LB cultures supplemented with chloramphenicol. BAC DNA was prepared using an Autogen 9600 robot. Each purified BAC DNA was subsequently transformed into the IS free MDS42recA host and approximately 384 colonies of each transformant were transferred to several duplicate Nylon membranes for hybridization screening with transposon specific probes.

In addition to the 45 independent BAC clones, three types of controls were also hybridized to membranes. These include a positive control (a) consisting of 384 individual *E. coli* DH10B colonies that did not contain any plasmid or BAC DNA. Two additional controls involved transformation of BAC DNA directly into the IS free MDS42recA strain, so that these BACs have never been grown in a bacterial host containing IS elements. The first of these controls (b) consisted of an approximately 150 kb BAC clone isolated from MDS42recA and subsequently re-transformed into the same bacterial host, 384 colonies of which were then transferred to Nylon membranes for hybridization analysis. A final control (c) involved the same BAC DNA, but rather than directly transforming this DNA into the IS-free host, the BAC DNA was mixed with an extract of DH10B produced by the Autogen robot containing only host chromosomal DNA fragments. This mixture was then transformed into the IS-free host and 384 of the resulting transformants were arrayed on a Nylon membrane for hybridization analysis. These three controls test the ability of the analysis to differentiate IS elements present in host chromosomal DNA versus BAC or plasmid DNA (control a), the lack of IS elements in BAC DNA that has never been propagated in an IS containing host (control b), and whether IS elements can be transferred in vitro, or by co-transformation with linear chromosomal DNA that contains IS elements (control c). Altogether 48 BAC combinations were tested, including 45 samples and 3 controls by arraying approximately 384 transformants of each BAC onto Nylon membranes for a total of 18,046 hybridization targets.

Probes for each of six IS element classes known to be present in *E. coli* DH 10B were designed to test the Nylon membranes for the presence of IS elements within the BAC DNA. These probes were produced by synthesizing two overlapping complimentary oligonucleotides which, when annealed leave single stranded overhangs which can be subsequently filled using the Klenow fragment of DNA polymerase in the presence of radio-labeled nucleotides to produce high specific activity double stranded probes specific to the most highly conserved region of each of the six IS classes. The oligonucleotide and corresponding probe sequences are shown in Table 5.

TABLE 5

Probe designs for IS1, IS2, IS3, IS5, IS10 and IS186 family detection

| IS | Oligo | Primer sequence | Probe sequence |
|---|---|---|---|
| IS1 | IS1-Ova | 5'CTTATGAGCCTGCTGTCACCCTTT | 5'CTTATGAGCCTGCTGTCACC- |
| | IS1-OVb | 5'TCCATATCACCACGTCAAAGGGTG | CTTTGACGTGGTGATATGGA |
| IS2 | IS2-OVa | 5'GTGGCTGACGGATAATGGTTCATG | 5'GTGGCTGACGGATAATGGTT- |
| | IS2-OVb | 5'TTCATTAGCCCGGTAGCATGAACC | CATGCTACCGGGCTAATGAA |
| IS3 | IS3-OVa | 5'CAGACGTCTTCTGAACGTGAACTG | 5'CAGACGTCTTCTGAACGTGA- |
| | IS3-OVb | 5'TCTCGGTAGACATCTCCAGTTCAC | ACTGGAGATGTCTACCGAGA |
| IS5 | IS5-OVa | 5'GAGCAGATTCTGCCATGGCAAAAC | 5'GAGCAGATTCTGCCATGGCA- |
| | IS5-OVb | 5'CGATGACTTCCACCATGTTTTGCC | AAACATGGTGGAAGTCATCG |
| IS10 | IS10-OVa | 5'ATTGCGAGCTTCAGTCGCACTACA | 5'ATTGCGAGCTTCAGTCGCAC- |
| | IS10-OVb | 5'AGTAACAGAACGACCGTGTAGTGC | TACACGGTCGTTCTGTTACT |
| IS186 | IS186-OVa | 5'TTGCGTGCAAAGGAACCTGAACTC | 5'TTGCGTGCAAAGGAACCTGA- |
| | IS186-OVb | 5'ATATCCACGCTTTCGCGAGTTCAG | ACTCGCGAAAGCGTGGATAT |

Hybridizations, washes and probe stripping procedures were carried out under standard conditions (Current Protocols in Molecular Biology (1994) sections 2.9-2.10). Each membrane was probed with a mixture of all six labeled probes and by each probe individually. Results are summarized in Table 6.

TABLE 6

Frequency of IS contamination in individual BAC library clones

| | Clone Name | Number of subclones | IS1 | IS2 | IS5 | IS10 | IS186 |
|---|---|---|---|---|---|---|---|
| 1 | C12_RP_4_V2(73)A1 | 369 | 1 | 14 | 1 | 11 | 0 |
| 2 | C22_RP_1_V2(107)A1 | 369 | 1 | 10 | 2 | 5 | 0 |
| 3 | CX_RP_3_V2(111)K1 | 377 | 2 | 5 | 0 | 13 | 10 |
| 4 | C12_RP_2_V2(71)A1 | 384 | 1 | 1 | 0 | 5 | 20 |
| 5 | C10_RP_3_V2(62)A1 | 384 | 1 | 11 | 4 | 11 | 0 |
| 6 | C2_RP_7_V2(15)A1 | 378 | 2 | 0 | 0 | 2 | 0 |
| 7 | C1_RP_5_V2(5)A1 | 378 | 0 | 0 | 0 | 2 | 0 |
| 8 | C22_RP_1_V2(107)K1 | 378 | 1 | 7 | 4 | 10 | 0 |
| 9 | C5_RP_3_V2(32)A1 | 384 | 3 | 10 | 1 | 1 | 0 |
| 10 | C5_RP_7_V2(36)A1 | 384 | 0 | 5 | 0 | 0 | 0 |
| 11 | C6_RP_5_V2(42)A1 | 377 | 17 | 2 | 0 | 1 | 0 |
| 12 | C5_RP_7_V2(36)I1 | 380 | 0 | 0 | 0 | 1 | 0 |
| 13 | C12_RP_4_V2(73)C1 | 368 | 0 | 2 | 0 | 3 | 0 |
| 14 | C5_RP_3_V2(32)I1 | 368 | 0 | 6 | 0 | 15 | 0 |
| 15 | CX_RP_3_V2(111)C1 | 367 | 0 | 6 | 1 | 11 | 23 |
| 16 | C4_RP_3_V2(26)I1 | 304 | 1 | 4 | 0 | 186 | 1 |
| 17 | C10_RP_3_V2(62)C1 | 379 | 0 | 0 | 0 | 0 | 0 |
| 18 | C2_RP_7_V2(15)C1 | 377 | 0 | 2 | 0 | 2 | 0 |
| 19 | C1_RP_5_V2(5)C1 | 380 | 2 | 10 | 2 | 5 | 33 |
| 20 | C4_RP_3_V2(26)C1 | 380 | 2 | 52 | 0 | 14 | 0 |
| 21 | C22_RP_1_V2(107)A1 | 375 | 0 | 12 | 0 | 1 | 6 |
| 22 | C12_RP_4_V2(73)I1 | 379 | 4 | 15 | 2 | 4 | 0 |
| 23 | Control a (1A5 in DH10B) | 384 | 0 | 0 | 0 | 0 | 0 |
| 24 | C9_RP_3_V2(57)C1 | 371 | 1 | 35 | 0 | 2 | 0 |
| 25 | C12_RP_4_V2(73)E1 | 383 | 10 | 31 | 0 | 14 | 3 |
| 26 | C22_RP1_1_V2(107)E1 | 379 | 1 | 10 | 1 | 27 | 0 |
| 27 | CX_RP_3_V2(111)E1 | 382 | 0 | 11 | 1 | 33 | 0 |
| 28 | C12_RP_2_V2(71)E1 | 384 | 1 | 6 | 0 | 6 | 0 |
| 29 | C10_RP_3_V2(62)E1 | 381 | 4 | 9 | 1 | 7 | 0 |
| 30 | C2_RP_7_V2(15)E1 | 383 | 0 | 11 | 0 | 5 | 0 |
| 31 | C1_RP_5_V2(5)E1 | 384 | 1 | 3 | 1 | 1 | 0 |
| 32 | C4_RP_3_V2(26)E1 | 382 | 2 | 14 | 1 | 8 | 0 |
| 33 | C5_RP_3_V2(32)E1 | 382 | 6 | 7 | 0 | 4 | 0 |
| 34 | C5_RP_7_V2(36)E1 | 351 | 4 | 4 | 6 | 14 | 0 |
| 35 | C6_RP_5_V2(42)E1 | 380 | 2 | 12 | 0 | 1 | 3 |
| 36 | C9_RP_3_V2(57)E1 | 381 | 6 | 15 | 5 | 16 | 5 |
| 37 | C12_RP_4_V2(73)G1 | 382 | 0 | 7 | 0 | 1 | 0 |
| 38 | Control b (1A5 in MDS42) | 382 | 0 | 0 | 0 | 0 | 0 |
| 39 | CX_RP_3_V2(111)G1 | 384 | 5 | 8 | 2 | 14 | 0 |
| 40 | C12_RP_2_V2(71)G1 | 384 | 3 | 6 | 1 | 9 | 0 |
| 41 | C10_RP_3_V2(62)G1 | 384 | 2 | 13 | 6 | 6 | 10 |
| 42 | C2_RP_7_V2(15)G1 | 382 | 1 | 29 | 0 | 4 | 17 |
| 43 | C1_RP_5_V2(5)G1 | 376 | 2 | 11 | 0 | 6 | 0 |
| 44 | C4_RP_3_V2(26)G1 | 379 | 2 | 379 | 3 | 29 | 4 |
| 45 | C5_RP_3_V2(32)G1 | 345 | 4 | 5 | 0 | 2 | 2 |
| 46 | C5_RP_7_V2(36)G1 | 374 | 1 | 20 | 4 | 0 | 1 |
| 47 | C6_RP_5_V2(42)G1 | 364 | 4 | 3 | 0 | 5 | 1 |
| 48 | Control c (1A5 in MDS42 + DH10B DNA) | 384 | 0 | 0 | 0 | 0 | 0 |

The lack of hybridization signal in any of the control hybridizations (clones 23, 38 and 48 in the table above) indicates that (a) DH 10B chromosomal DNA containing IS elements is not present in detectable quantities on the membranes, (b) no IS elements are present in DNA propagated solely in the IS-free strain MDS42recA and (c) no IS elements are transferred from DH10B chromosomal DNA to the BAC DNA in the course of the transformation procedure. The presence of IS elements in all but one (clone 17, BAC C10_RP__3_V2(62)C1) of the BACs isolated from DH10B, indicates that the hybridization strategy is an effective method for detecting IS elements on these membranes and that IS contamination is common in BACs propagated on strains containing IS elements. Together these data demonstrate that BAC libraries maintained in IS free bacterial hosts remain free of IS elements and therefore represent a superior technology for producing and maintaining BAC libraries.

In addition, IS free bacterial hosts can also be used to identify and isolate IS-free BACs from existing libraries by the transformation, arraying and probing strategy outlined in this example. For example, each of the 45 DH10B derived clones listed in Table 6 contains IS contaminated progeny as well as IS free progeny and the use of an IS free host, coupled with the hybridization screening strategy described here not only identifies, but also isolates, IS free clones from clones contaminated with IS elements. The resulting IS-free library would obviously be superior to the contaminated variant produced from IS containing bacteria.

EXAMPLE 8

Cloning of a Difficult to Clone Sequence in Strains Lacking IS Elements

Figure 5:
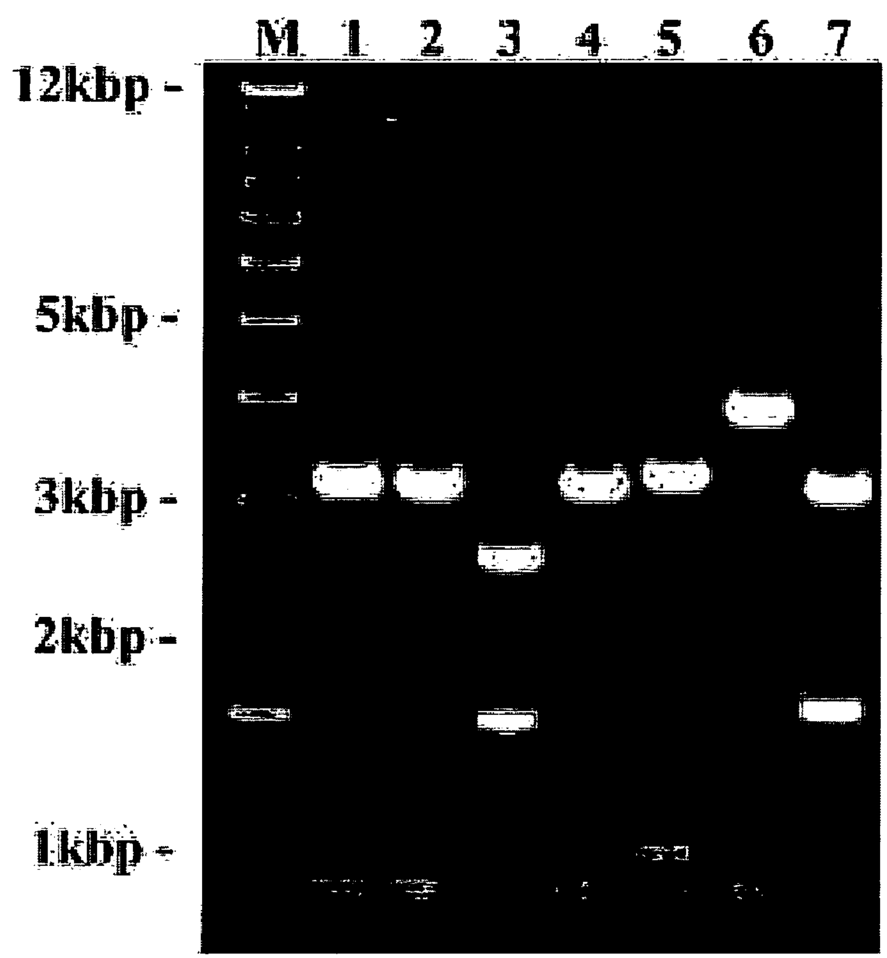
FIG. 5 shows the restriction pattern of pCTXVP60 propagated in various strains: (M) molecular weight marker, 1 kbp ladder; (1) MDS41, no insertion; (2) MDS42, no insertion; (3) DH10B, IS10 insertion; (4) DH10B, IS10 insertion/deletion; (5) C600, IS5 insertion; (6) C600 IS1 insertion; and (7) C600, IS1 insertion. Relative positions of the IS insertions in the CTXVP60 reading frame are diagrammed below the gel.
Figure 5:
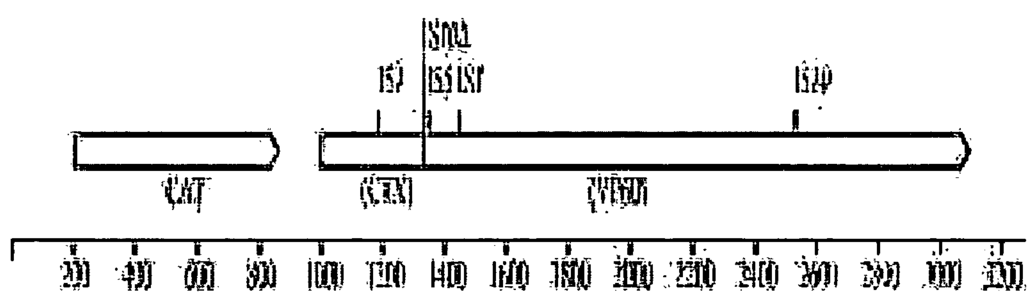

Attempts to clone the open reading frame encoding the VP60 of rabbit haemorrhagic disease virus fused to the B subunit of cholera toxin ("CTXVP60 fusion construct") using standard strains of bacteria have been unsuccessful. By providing a strain lacking IS elements, the CTXVP60 fusion construct was capable of being cloned. The surprising efficiency with which the CTXVP60 fusion construct was cloned in the strain lacking IS elements indicates that the presence of IS elements in the host chromosomal or extrachromosomal nucleic acids may be the primary obstacle to cloning such toxic genes. MDS42 was used to prepare pCTXVP60, carrying the CTXVP60 open reading frame. The plasmid DNA was then propagated in various hosts, isolated, then digested with NcoI and EcoRI. FIG. 5 shows a representative restriction pattern. The fragments were then purified and sequenced. MDS41 (lane 1) and MDS42 (lane 2) did not contain any insertion sequences. Plasmid DNA from DH10B contained an IS1 insertion (lane 3) and also an IS10 insertion/deletion (lane 4). Plasmid DNA from strain C600 contained an IS5 insertion (lane 5), and an IS1 insertion (lanes 6 and 7). This shows that strains lacking IS elements may be used to clone sequences that would be difficult to clone (e.g., toxic genes) in other strains.

EXAMPLE 9

Detection of IS Contamination of the Genome of a Host Carrying a Toxic Gene

Figure 6:
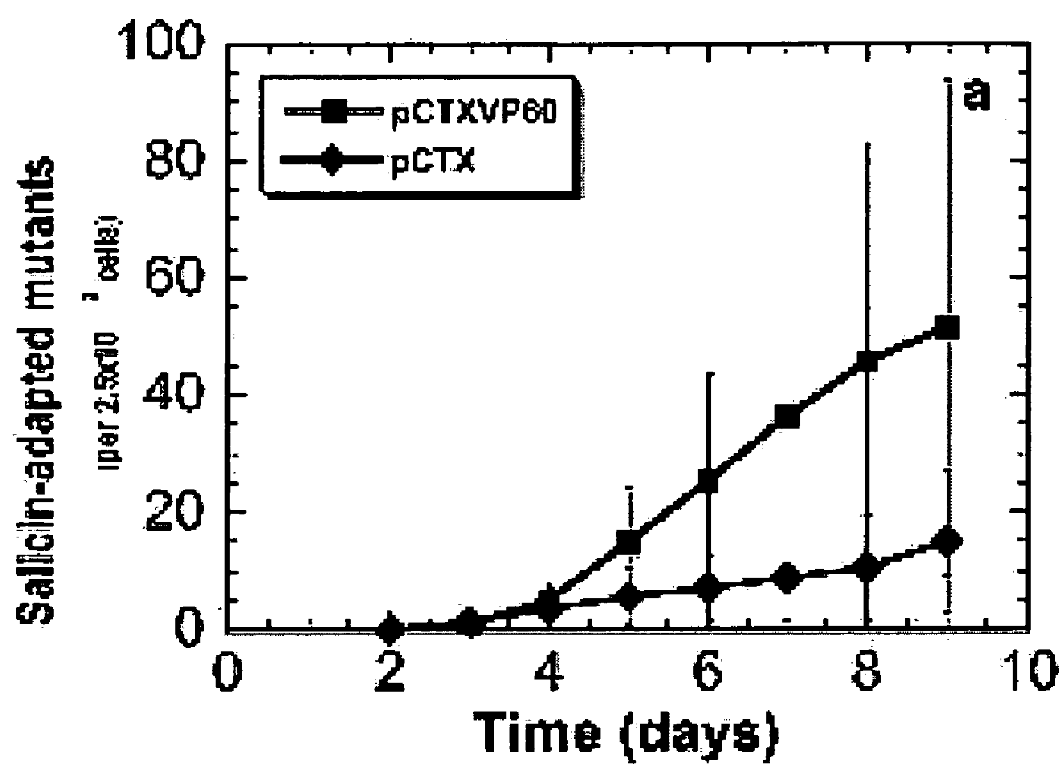
FIG. 6 compares the frequency of mutation by IS hopping to the genome in MG1655 transformed with either pCTXVP60 or pCTX as measured by the acquired ability to utilize salicin as a carbon source.

Bystander mutation tests were performed on MG1655 transformed with pCTXVP60. Briefly, MG1655 cells were electroporated with either pCTX, carrying the CTX open reading frame (MG1655(pCTX)), or the toxic construct pCTXVP60 (MG1655(pCTXVP60)) and the cultures were grown to saturation, followed by spreading on salicin/minimal plates. New colonies (adaptive mutants) were marked and counted daily. The data shown in FIG. 6 were derived from five replicate experiments. Total plated cell numbers were calculated by plating appropriate dilutions from 2-5 parallel cultures onto rich medium. The mean colony numbers were normalized to $2.5\times10^9$ cells. A two-factor ANOVA analysis ($\alpha\leqq0.05$) with post-hoc (t-tests) was used to determine if the adaptation rates (the mutant number/day) were significant with respect to strain or time. Both the time and strain/plasmid were determined to be significant ($p\leqq0.001$). The interaction of time and strain/plasmid was determined not to be significant. Counting the mutant colonies appearing on the plates revealed a>4-fold increase in the mutation rate due to pCTXVP60 (FIG. 6). Most of the bgl mutants of MG1655(pCTXVP60) also carry insertions in the plasmid.

EXAMPLE 10

Effect of Protein Overexpression on the Mutational Spectrum

Figure 7:
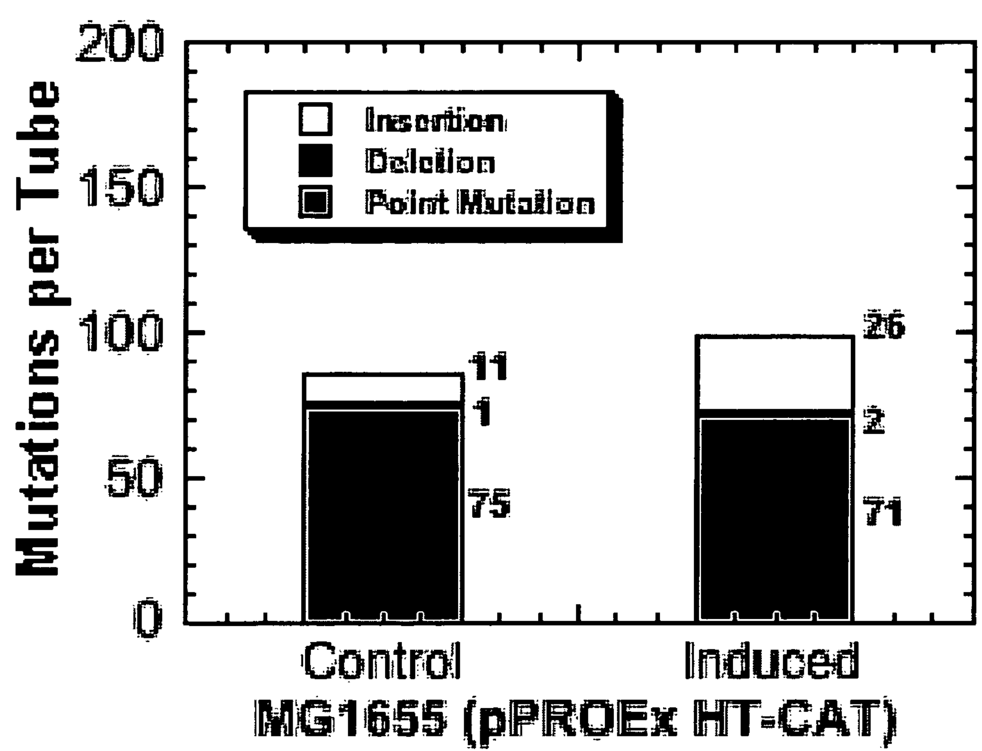
FIG. 7 compares the rate of IS hopping in MG1655 carrying an expression plasmid for CAT in the presence and absence of IPTG induction, as measured by the appearance of D-cycloserine mutants. D-cycloserine mutants result almost exclusively from loss-of-function mutations in cycA.

Cultures of MG1655 carrying an expression plasmid for the well tolerated CAT enzyme were compared with and without IPTG induction. Using fluctuation tests, a 2.5-fold increase in IS transposition rates into cycA in cultures derived from IPTG-treated cells was found. Insertions involving IS1, IS2, IS5 and IS150 were observed, while point mutation rates remained virtually unchanged. (FIG. 7). This indicates that the over-expression of recombinant proteins may induce IS transposition. The strains lacking IS elements may therefore be a more stable host for protein production.

EXAMPLE 11

Figure 8:
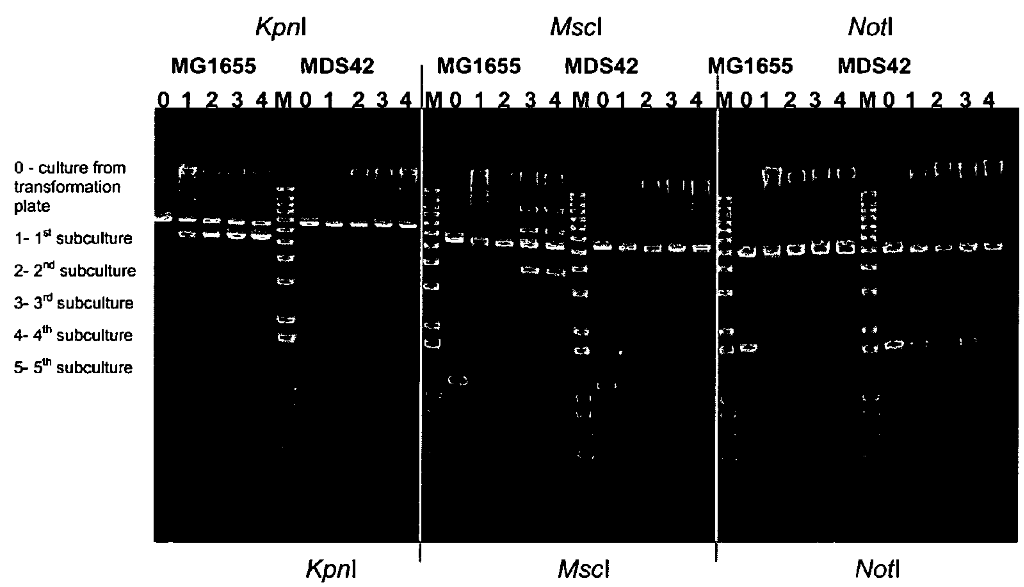
FIG. 8 shows the restriction pattern of pT-ITR propagated in MDS42 and MG1655.

Cloning of a Difficult to Clone Plasmid that Does Not Encode a Protein Product in a Strain Lacking IS Elements The plasmid pT-ITR, which contains a pair of G-C rich hairpins known as "hammerheads," which are thermodynamically very stable, was propagated for 4 serial passages with a $10^6$ dilution on each passage, in strains MDS42 and MG1655. FIG. 8 illustrates that 9T-ITR can be propagated intact for at least 4 serial passages in MDS42. However, 9T-ITR in the undeleted parent strain MG1655 is subject to deletion and rearrangement within the first passage.

TABLE 2

| Strain | Type | Coordinates | Name | B | Function |
|---|---|---|---|---|---|
| MDS01 | CDS | complement(262552 . . . 262893) | | b0245 | orf, hypothetical protein |
| MDS01 | CDS | complement(262914 . . . 263231) | yafW | b0246 | orf, hypothetical protein |
| MDS01 | CDS | complement(263480 . . . 263956) | ykfG | b0247 | putative DNA repair protein |
| MDS01 | CDS | complement(263972 . . . 264430) | yafX | b0248 | orf, hypothetical protein |
| MDS01 | CDS | complement(264528 . . . 264767) | ykfF | b0249 | orf, hypothetical protein |
| MDS01 | CDS | complement(264844 . . . 265311) | ykfB | b0250 | orf, hypothetical protein |
| MDS01 | CDS | complement(265334 . . . 266191) | yafY | b0251 | hypothetical transcriptional regulator |
| MDS01 | CDS | complement(266408 . . . 267244) | yafZ | b0252 | orf, hypothetical protein |
| MDS01 | CDS | complement(267321 . . . 268187) | ykfA | b0253 | putative GTP-binding protein |
| MDS01 | CDS | complement(268513 . . . 269406) | perR | b0254 | peroxide resistance protein |
| MDS01 | CDS | 269466 . . . 269870 | yi91a | b0255 | |
| MDS01 | CDS | 269827 . . . 270978 | tra8_1 | b0256 | IS30 transposase |
| MDS01 | CDS | 271054 . . . 271479 | | b0257 | putative transposase |
| MDS01 | CDS | 272086 . . . 273216 | ykfC | b0258 | orf, hypothetical protein |
| MDS01 | CDS | complement(273325 . . . 274341) | trs5_1 | b0259 | IS5 transposase |
| MDS01 | CDS | 274525 . . . 275952 | ykfB | b0260 | orf, hypothetical protein |
| MDS01 | CDS | 275939 . . . 276871 | yafY | b0261 | hypothetical transcriptional regulator |
| MDS01 | CDS | complement(276980 . . . 278038) | afuC | b0262 | putative ATP-binding component of a transport system |
| MDS01 | CDS | complement(278038 . . . 278400) | | b0263 | |
| MDS01 | CDS | complement(278402 . . . 278905) | insB_2 | b0264 | IS1 protein InsB |
| MDS01 | CDS | complement(278824 . . . 279099) | insA_2 | b0265 | IS1 protein InsA |
| MDS01 | CDS | complement(279609 . . . 279986) | yagB | b0266 | orf, hypothetical protein |
| MDS01 | CDS | complement(280053 . . . 281207) | yagA | b0267 | orf, hypothetical protein |
| MDS01 | CDS | 281481 . . . 282410 | yagE | b0268 | putative lyase/synthase |
| MDS01 | CDS | 282425 . . . 284392 | yagF | b0269 | putative dehydratase |
| MDS01 | CDS | 284619 . . . 286001 | yagG | b0270 | putative permease |
| MDS01 | CDS | 286013 . . . 287623 | yagH | b0271 | putative beta-xylosidase (EC 3.2.1.37 |
| MDS01 | CDS | complement(287628 . . . 288386) | yagI | b0272 | putative regulator |
| MDS01 | CDS | complement(288525 . . . 289529) | argF | b0273 | ornithine carbamoyltransferase 2, chain F |

TABLE 2-continued

| Strain | Type | Coordinates | Name | B | Function |
|---|---|---|---|---|---|
| MDS01 | CDS | complement(289873 . . . 290376) | insB_3 | b0274 | IS1 protein InsB |
| MDS01 | CDS | complement(290295 . . . 290570) | insA_3 | b0275 | IS1 protein InsA |
| MDS01 | CDS | 290724 . . . 291455 | yagJ | b0276 | orf, hypothetical protein |
| MDS01 | CDS | complement(291546 . . . 292172) | yagK | b0277 | orf, hypothetical protein |
| MDS01 | CDS | complement(292444 . . . 293142) | yagL | b0278 | DNA-binding protein |
| MDS01 | CDS | complement(293169 . . . 294023) | yagM | b0279 | orf, hypothetical protein |
| MDS01 | CDS | complement(294363 . . . 294803) | yagN | b0280 | orf, hypothetical protein |
| MDS01 | CDS | complement(294920 . . . 296320) | intF | b0281 | putative phage integrase |
| MDS01 | CDS | complement(296605 . . . 297015) | yagP | b0282 | putative transcriptional regulator LYSR-type |
| MDS01 | CDS | complement(296994 . . . 297950) | yagQ | b0283 | orf, hypothetical protein |
| MDS01 | CDS | complement(297960 . . . 300158) | yagR | b0284 | orf, hypothetical protein |
| MDS01 | CDS | complement(300155 . . . 301111) | yagS | b0285 | orf, hypothetical protein |
| MDS01 | CDS | complement(301108 . . . 301797) | yagT | b0286 | putative xanthine dehydrogenase (EC 1.1.1.20 |
| MDS01 | CDS | 302215 . . . 302829 | yagU | b0287 | orf, hypothetical protein |
| MDS01 | CDS | complement(303077 . . . 303406) | ykgJ | b0288 | putative ferredoxin |
| MDS01 | CDS | complement(303719 . . . 304474) | yagV | b0289 | orf, hypothetical protein |
| MDS01 | CDS | complement(304398 . . . 306041) | yagW | b0290 | putative receptor |
| MDS01 | CDS | complement(306031 . . . 308556) | yagX | b0291 | putative enzyme |
| MDS01 | CDS | complement(308582 . . . 309250) | yagY | b0292 | orf, hypothetical protein |
| MDS01 | CDS | complement(309308 . . . 309895) | yagZ | b0293 | orf, hypothetical protein |
| MDS01 | CDS | complement(309970 . . . 310560) | ykgK | b0294 | putative regulator |
| MDS01 | CDS | 311336 . . . 311563 | ykgL | b0295 | orf, hypothetical protein |
| MDS01 | CDS | complement(311738 . . . 312001) | ykgM | b0296 | putative ribosomal protein |
| MDS01 | CDS | 313581 . . . 314468 | eaeH | b0297 | attaching and effacing protein, pathogenesis factor |
| MDS01 | CDS | 314506 . . . 314814 | | b0298 | |
| MDS01 | CDS | 314811 . . . 315677 | tra5_5 | b0299 | |
| MDS01 | CDS | complement(315674 . . . 316393) | ykgA | b0300 | putative ARAC-type regulatory protein |
| MDS01 | CDS | complement(316950 . . . 317552) | ykgB | b0301 | orf, hypothetical protein |
| MDS01 | CDS | complement(317555 . . . 317806) | ykgI | b0303 | orf, hypothetical protein |
| MDS01 | CDS | complement(317900 . . . 319252) | ykgC | b0304 | putative oxidoreductase |
| MDS01 | CDS | 319451 . . . 320305 | ykgD | b0305 | putative ARAC-type regulatory protein |
| MDS01 | CDS | 320832 . . . 321551 | ykgE | b0306 | putative dehydrogenase subunit |
| MDS01 | CDS | 321562 . . . 322989 | ykgF | b0307 | orf, hypothetical protein |
| MDS01 | CDS | 322829 . . . 323677 | ykgG | b0308 | putative transporter |
| MDS01 | CDS | complement(323632 . . . 323844) | | b0309 | orf, hypothetical protein |
| MDS01 | CDS | complement(323920 . . . 324588) | ykgH | b0310 | orf, hypothetical protein |
| MDS02 | CDS | complement(1398271 . . . 1399803) | ydaH | b1336 | |
| MDS02 | CDS | complement(1399834 . . . 1401279) | | b1337 | |
| MDS02 | CDS | complement(1401279 . . . 1402604) | ydaJ | b1338 | |
| MDS02 | CDS | 1402765 . . . 1403673 | ydaK | b1339 | putative transcriptional regulator LYSR-type |
| MDS02 | CDS | 1404003 . . . 1404566 | ydaL | b1340 | orf, hypothetical protein |
| MDS02 | CDS | complement(1404587 . . . 1405879) | | b1341 | orf, hypothetical protein |
| MDS02 | CDS | 1406074 . . . 1407057 | | b1342 | orf, hypothetical protein |
| MDS02 | CDS | 1407535 . . . 1408908 | dbpA | b1343 | ATP-dependent RNA helicase |
| MDS02 | CDS | complement(1409037 . . . 1409972) | ydaO | b1344 | orf, hypothetical protein |
| MDS02 | CDS | complement(1410024 . . . 1411259) | | b1345 | |
| MDS02 | CDS | complement(1411261 . . . 1411500) | ydaQ | b1346 | putative lambdoid prophage Rac excisionase |
| MDS02 | CDS | complement(1411555 . . . 1411764) | ydaC | b1347 | orf, hypothetical protein |
| MDS02 | CDS | complement(1411757 . . . 1411951) | lar | b1348 | restriction alleviation and modification enhancement |
| MDS02 | CDS | complement(1412008 . . . 1412817) | recT | b1349 | recombinase, DNA renaturation |
| MDS02 | CDS | complement(1412810 . . . 1415410) | recE | b1350 | exonuclease VIII, ds DNA exonuclease 5'--> 3' specific |
| MDS02 | CDS | complement(1415512 . . . 1415787) | racC | b1351 | RacC protein |
| MDS02 | CDS | complement(1416032 . . . 1416265) | kil | b1352 | Kil protein (killing function) of lambdoid prophage Rac |
| MDS02 | CDS | 1416572 . . . 1417183 | sieB | b1353 | phage superinfection exclusion protein |
| MDS02 | CDS | 1417192 . . . 1417368 | | b1354 | orf, hypothetical protein |
| MDS02 | CDS | complement(1417346 . . . 1417525) | | b1355 | orf, hypothetical protein |
| MDS02 | CDS | complement(1417789 . . . 1418265) | ydaR | b1356 | |
| MDS02 | CDS | 1418389 . . . 1418685 | ydaS | b1357 | orf, hypothetical protein |
| MDS02 | CDS | 1418708 . . . 1419130 | ydaT | b1358 | orf, hypothetical protein |
| MDS02 | CDS | 1419143 . . . 1420000 | ydaU | b1359 | orf, hypothetical protein |
| MDS02 | CDS | 1420007 . . . 1420753 | | b1360 | putative DNA replication factor |
| MDS02 | CDS | 1420725 . . . 1421336 | ydaW | b1361 | orf, hypothetical protein |
| MDS02 | CDS | 1421363 . . . 1421668 | | b1362 | putative Rac prophage endopeptidase |
| MDS02 | CDS | 1421806.1423263 | trkG | b1363 | |
| MDS02 | CDS | 1423202 . . . 1423483 | | b1364 | orf, hypothetical protein |
| MDS02 | CDS | 1423401 . . . 1423664 | | b1365 | orf, hypothetical protein |
| MDS02 | CDS | 1423645 . . . 1424004 | ydaY | b1366 | orf, hypothetical protein |
| MDS02 | CDS | 1424079 . . . 1424312 | | b1367 | orf, hypothetical protein |
| MDS02 | CDS | 1424478 . . . 1425506 | | b1368 | putative alpha helix protein |
| MDS02 | CDS | 1425482 . . . 1425637 | | b1369 | orf, hypothetical protein |
| MDS02 | CDS | complement(1425770 . . . 1426750) | trs5_5 | b1370 | |
| MDS02 | CDS | 1426547 . . . 1427008 | | b1371 | orf, hypothetical protein |

TABLE 2-continued

| Strain | Type | Coordinates | Name | B | Function |
|---|---|---|---|---|---|
| MDS02 | CDS | 1427067 . . . 1430435 | | b1372 | |
| MDS02 | CDS | 1430435 . . . 1431010 | | b1373 | tail fiber assembly protein homolog from lambdoid prophage Rac |
| MDS02 | CDS | complement(1431108 . . . 1431698) | | b1374 | |
| MDS02 | CDS | complement(1432015 . . . 1432281) | ynaE | b1375 | orf, hypothetical protein |
| MDS02 | CDS | complement(1433209 . . . 1433715) | | b1376 | ynaF putative filament protein |
| MDS02 | CDS | complement(1433784 . . . 1434917) | | b1377 | |
| MDS02 | CDS | complement(1435284 . . . 1438808) | ydbK | b1378 | putative oxidoreductase, Fe—S subunit |
| MDS02 | CDS | complement(1439345 . . . 1439767) | hslJ | b1379 | heat shock protein HslJ |
| MDS02 | CDS | complement(1439878 . . . 1440867) | ldhA | b1380 | fermentative D-lactate dehydrogenase NAD-dependent |
| MDS02 | CDS | 1441075 . . . 1443714 | ydbH | b1381 | orf, hypothetical protein |
| MDS02 | CDS | 1443711 . . . 1443896 | ynbE | b1382 | orf, hypothetical protein |
| MDS02 | CDS | 1443898 . . . 1444230 | ydbL | b1383 | orf, hypothetical protein |
| MDS02 | CDS | complement(1444402 . . . 1445307) | feaR | b1384 | regulatory protein for 2-phenylethylamine catabolism |
| MDS02 | CDS | 1445540 . . . 1447042 | feaB | b1385 | phenylacetaldehyde dehydrogenase |
| MDS02 | CDS | complement(1447100 . . . 1449373) | tynA | b1386 | copper amine oxidase (tyramine oxidase) |
| MDS02 | CDS | complement(1449621 . . . 1451666) | maoC | b1387 | |
| MDS02 | CDS | 1451951 . . . 1452880 | ydbO | b1388 | |
| MDS02 | CDS | 1452892 . . . 1453179 | ynbF | b1389 | |
| MDS02 | CDS | 1453188 . . . 1453934 | ydbP | b1390 | |
| MDS02 | CDS | 1453943 . . . 1454446 | | b1391 | |
| MDS02 | CDS | 1454454 . . . 1455524 | | b1392 | |
| MDS02 | CDS | 1455521 . . . 1456288 | ydbS | b1393 | |
| MDS02 | CDS | 1456288 . . . 1457076 | | b1394 | |
| MDS02 | CDS | 1457078 . . . 1458505 | ydbU | b1395 | |
| MDS02 | CDS | 1458495 . . . 1458917 | | b1396 | |
| MDS02 | CDS | 1458917 . . . 1460122 | | b1397 | |
| MDS02 | CDS | 1460149 . . . 1461462 | | b1398 | |
| MDS02 | CDS | 1461563 . . . 1462513 | | b1399 | |
| MDS02 | CDS | 1462495 . . . 1463085 | | b1400 | |
| MDS02 | CDS | 1463416 . . . 1465974 | ydbA_1 | b1401 | |
| MDS02 | CDS | complement(1465945 . . . 1466850) | yi22_2 | b1402 | IS2 hypothetical protein |
| MDS02 | CDS | complement(1466808 . . . 1467218) | yi21_2 | b1403 | IS2 hypothetical protein |
| MDS02 | CDS | 1467382 . . . 1468533 | tra8_2 | b1404 | IS30 transposase |
| MDS02 | CDS | 1468714 . . . 1472037 | ydbA_2 | b1405 | |
| MDS02 | CDS | 1472245 . . . 1473105 | ydbC | b1406 | putative dehydrogenase |
| MDS02 | CDS | 1473162 . . . 1475474 | ydbD | b1407 | orf, hypothetical protein |
| MDS02 | CDS | 1475639 . . . 1476250 | | b1408 | |
| MDS02 | CDS | 1476250 . . . 1477146 | | b1409 | putative phosphatidate cytidiltransferase |
| MDS02 | CDS | 1477162 . . . 1478919 | | b1410 | orf, hypothetical protein |
| MDS02 | CDS | 1478933 . . . 1480225 | ynbD | b1411 | putative enzymes |
| MDS02 | misc_RNA | complement(1403676 . . . 1403833) | IS061 | b4426 | |
| MDS02 | misc_RNA | 1435145 . . . 1435252 | tke8 | b4427 | |
| MDS03 | CDS | complement(2555340 . . . 2556743) | eutB | b2441 | ethanolamine ammonia-lyase, heavy chain |
| MDS03 | CDS | 2556793 . . . 2558088 | | b2442 | putative prophage integrase |
| MDS03 | CDS | 2558279 . . . 2558920 | | b2443 | orf, hypothetical protein |
| MDS03 | CDS | 2559390 . . . 2559635 | | b2444 | orf, hypothetical protein |
| MDS03 | CDS | 2559632 . . . 2560015 | | b2445 | orf, hypothetical protein |
| MDS03 | CDS | 2560133 . . . 2560549 | | b2446 | orf, hypothetical protein |
| MDS03 | CDS | 2560546 . . . 2561139 | | b2447 | orf, hypothetical protein |
| MDS03 | CDS | 2561599 . . . 2561991 | | b2448 | orf, hypothetical protein |
| MDS03 | CDS | 2562002 . . . 2562394 | | b2449 | orf, hypothetical protein |
| MDS03 | CDS | 2562515 . . . 2563354 | | b2450 | orf, hypothetical protein |
| MDS04 | CDS | 2754181 . . . 2755422 | intA | b2622 | prophage CP4-57 integrase |
| MDS04 | CDS | complement(2755666 . . . 2756622) | yfjH | b2623 | putative histone |
| MDS04 | CDS | 2756666 . . . 2756878 | alpA | b2624 | prophage CP4-57 regulatory protein alpA |
| MDS04 | CDS | 2757007 . . . 2758416 | yfjI | b2625 | orf, hypothetical protein |
| MDS04 | CDS | 2758569 . . . 2759195 | yfjJ | b2626 | orf, hypothetical protein |
| MDS04 | CDS | complement(2759373 . . . 2761562) | yfjK | b2627 | orf, hypothetical protein |
| MDS04 | CDS | complement(2761559 . . . 2763175) | yfjL | b2628 | orf, hypothetical protein |
| MDS04 | CDS | complement(2763535 . . . 2763798) | yfjM | b2629 | orf, hypothetical protein |
| MDS04 | CDS | 2763940 . . . 2765013 | yfjN | b2630 | putative cell division protein |
| MDS04 | CDS | 2765057 . . . 2765377 | yfjO | b2631 | orf, hypothetical protein |
| MDS04 | CDS | 2765732 . . . 2766595 | yfjP | b2632 | putative GTP-binding protein |
| MDS04 | CDS | 2766687 . . . 2767508 | yfjQ | b2633 | orf, hypothetical protein |
| MDS04 | CDS | 2767725 . . . 2768426 | yfjR | b2634 | orf, hypothetical protein |
| MDS04 | CDS | 2768311 . . . 2768703 | | b2635 | orf, hypothetical protein |
| MDS04 | CDS | 2768454 . . . 2769146 | | b2636 | orf, hypothetical protein |
| MDS04 | CDS | 2769170 . . . 2769637 | yfjT | b2637 | orf, hypothetical protein |
| MDS04 | CDS | complement(2769862 . . . 2770176) | | b2638 | orf, hypothetical protein |
| MDS04 | CDS | complement(2770189 . . . 2770707) | | b2639 | putative pump protein |
| MDS04 | CDS | complement(2770858 . . . 2771058) | | b2640 | orf, hypothetical protein |
| MDS04 | CDS | complement(2770998 . . . 2771114) | | b2641 | orf, hypothetical protein |
| MDS04 | CDS | 2771340 . . . 2773043 | yfjW | b2642 | orf, hypothetical protein |
| MDS04 | CDS | 2773941 . . . 2774399 | yfjX | b2643 | orf, hypothetical protein |
| MDS04 | CDS | 2774408 . . . 2774890 | yfjY | b2644 | putative DNA repair protein |

TABLE 2-continued

| Strain | Type | Coordinates | Name | B | Function |
|---|---|---|---|---|---|
| MDS04 | CDS | 2775137 . . . 2775454 | yfjZ | b2645 | orf, hypothetical protein |
| MDS04 | CDS | 2775475 . . . 2775804 | ypjF | b2646 | orf, hypothetical protein |
| MDS04 | CDS | complement(2776168 . . . 2780877) | ypjA | b2647 | putative ATP-binding component of a transport system |
| MDS04 | CDS | complement(2781087 . . . 2781230) | | b2648 | orf, hypothetical protein |
| MDS04 | CDS | complement(2781660 . . . 2782451) | | b2649 | orf, hypothetical protein |
| MDS04 | CDS | complement(2782551 . . . 2783033) | | b2650 | orf, hypothetical protein |
| MDS04 | CDS | 2783243 . . . 2783374 | | b2651 | orf, hypothetical protein |
| MDS04 | tRNA | complement(2783784 . . . 2783859) | ileY | b2652 | tRNA-Ile |
| MDS04 | CDS | complement(2783822 . . . 2783995) | | b2653 | orf, hypothetical protein |
| MDS04 | CDS | 2784419 . . . 2784751 | | b2654 | orf, hypothetical protein |
| MDS04 | CDS | 2785628 . . . 2786260 | | b2657 | putative enzyme |
| MDS04 | CDS | 2786399 . . . 2786671 | | b2658 | orf, hypothetical protein |
| MDS04 | CDS | 2786902 . . . 2787984 | | b2659 | orf, hypothetical protein |
| MDS04 | CDS | 2787938 . . . 2789272 | ygaF | b2660 | orf, hypothetical protein |
| MDS04 | CDS | 2784770 . . . 2785456 | ygaR | b4462 | orf, hypothetical protein |
| MDS05 | CDS | complement(2064329 . . . 2065345) | trs5_6 | b1994 | IS5 transposase |
| MDS05 | CDS | 2066632 . . . 2067051 | | b1995 | orf, hypothetical protein |
| MDS05 | CDS | complement(2066976 . . . 2067881) | yi22_3 | b1996 | IS2 hypothetical protein |
| MDS05 | CDS | complement(2067839 . . . 2068249) | yi21_3 | b1997 | IS2 hypothetical protein |
| MDS05 | CDS | 2068268 . . . 2068528 | | b1998 | orf, hypothetical protein |
| MDS05 | CDS | 2068525 . . . 2069235 | yeeP | b1999 | putative histone |
| MDS05 | CDS | 2069563 . . . 2072682 | flu | b2000 | antigen 43, phase-variable bipartite outer membrane fluffing protein |
| MDS05 | CDS | 2072797 . . . 2074335 | | b2001 | orf, hypothetical protein |
| MDS05 | CDS | 2074332 . . . 2074778 | yeeS | b2002 | putative DNA repair protein, RADC family |
| MDS05 | CDS | 2074841 . . . 2075062 | yeeT | b2003 | orf, hypothetical protein |
| MDS05 | CDS | 2075136 . . . 2075504 | yeeU | b2004 | putative structural protein |
| MDS05 | CDS | 2075593 . . . 2075967 | yeeV | b2005 | orf, hypothetical protein |
| MDS05 | CDS | 2075964 . . . 2076158 | yeeW | b2006 | orf, hypothetical protein |
| MDS05 | CDS | complement(2077056 . . . 2077451) | veeX | b2007 | putative alpha helix protein |
| MDS05 | CDS | complement(2077557 . . . 2078615) | yeeA | b2008 | orf, hypothetical protein |
| MDS05 | misc_RNA | 2069339 . . . 2069542 | | b4435 | IS102 |
| MDS06 | CDS | complement(3451530 . . . 3451949) | | b3322 | calcium-binding protein required for initiation of chromosome replication |
| MDS06 | CDS | complement(3451951 . . . 3453420) | yheD | b3323 | putative export protein A for general secretion pathway (GSP) |
| MDS06 | CDS | 3453600 . . . 3454415 | yheE | b3324 | |
| MDS06 | CDS | 3454387 . . . 3456351 | yheF | b3325 | |
| MDS06 | CDS | 3456361 . . . 3457842 | yheG | b3326 | |
| MDS06 | CDS | 3457839 . . . 3459035 | hofF | b3327 | |
| MDS06 | CDS | 3459045 . . . 3459482 | hofG | b3328 | |
| MDS06 | CDS | 3459490 . . . 3459999 | hofH | b3329 | |
| MDS06 | CDS | 3459957 . . . 3460373 | yheH | b3330 | |
| MDS06 | CDS | 3460366 . . . 3460953 | yheI | b3331 | |
| MDS06 | CDS | 3460946 . . . 3461929 | yheJ | b3332 | |
| MDS06 | CDS | 3461941 . . . 3463107 | yheK | b3333 | |
| MDS06 | CDS | 3463080 . . . 3463565 | pshM | b3334 | |
| MDS06 | CDS | 3463565 . . . 3464242 | hofD | b3335 | |
| MDS06 | CDS | complement(3464271 . . . 3464747) | bfr | b3336 | bacterioferrin, an iron storage homoprotein |
| MDS06 | CDS | complement(3464819 . . . 3465013) | yheA | b3337 | |
| MDS06 | CDS | complement(3465182 . . . 3467875) | yheB | b3338 | |
| MDS07 | CDS | 2464567 . . . 2465724 | intC | b2349 | |
| MDS07 | CDS | 2465877 . . . 2466239 | | b2350 | |
| MDS07 | CDS | 2471542 . . . 2471988 | | b2350 | orf, hypothetical protein |
| MDS07 | CDS | 2466236 . . . 2467156 | | b2351 | |
| MDS07 | CDS | 2467153 . . . 2468484 | | b2352 | putative ligase |
| MDS07 | CDS | 2468783 . . . 2469127 | | b2353 | |
| MDS07 | CDS | complement(2469099 . . . 2469539) | | b2354 | orf, hypothetical protein |
| MDS07 | CDS | complement(2469566 . . . 2470084) | yfdL | b2355 | putative RNA polymerase beta |
| MDS07 | CDS | complement(2470134 . . . 2470442) | yfdM | b2356 | orf, hypothetical protein |
| MDS07 | CDS | complement(2470409 . . . 2470903) | yfdN | b2357 | orf, hypothetical protein |
| MDS07 | CDS | complement(2470900 . . . 2471268) | yfdO | b2358 | orf, hypothetical protein |
| MDS07 | CDS | 2472054 . . . 2472878 | | b2360 | orf, hypothetical protein |
| MDS07 | CDS | 2472979 . . . 2473542 | | b2361 | orf, hypothetical protein |
| MDS07 | CDS | 2473533 . . . 2473895 | | b2362 | orf, hypothetical protein |
| MDS07 | CDS | 2473895 . . . 2474200 | | b2363 | orf, hypothetical protein |
| MDS08 | CDS | 1625541 . . . 1626287 | ydfG | b1539 | putative oxidoreductase |
| MDS08 | CDS | 1626376 . . . 1627062 | ydfH | b1540 | orf, hypothetical protein |
| MDS08 | CDS | 1627239 . . . 1627442 | | b1541 | orf, hypothetical protein |
| MDS08 | CDS | complement(1627477 . . . 1628937) | ydfI | b1542 | putative oxidoreductase |
| MDS08 | CDS | complement(1629026 . . . 1630309) | | b1543 | putative transport protein |
| MDS08 | CDS | 1631063 . . . 1631329 | ydfK | b1544 | orf, hypothetical protein |
| MDS08 | CDS | 1631646 . . . 1632236 | | b1545 | |
| MDS08 | CDS | complement(1632334 . . . 1632909) | ydfM | b1546 | tail fiber assembly protein homolog from lambdoid prophage Qin |
| MDS08 | CDS | complement(1632909 . . . 1633871) | | b1547 | |

TABLE 2-continued

| Strain | Type | Coordinates | Name | B | Function |
|---|---|---|---|---|---|
| MDS08 | CDS | complement(1633822 . . . 1634391) | nohA | b1548 | DNA packaging protein NU1 homolog from lambdoid prophages |
| MDS08 | CDS | 1635056 . . . 1635481 | ydfO | b1549 | orf, hypothetical protein |
| MDS08 | CDS | complement(1635633 . . . 1635809) | | b1550 | |
| MDS08 | CDS | complement(1635978 . . . 1636169) | | b1551 | orf, hypothetical protein |
| MDS08 | CDS | complement(1636479 . . . 1636691) | cspI | b1552 | cold shock-like protein |
| MDS08 | CDS | complement(1637054 . . . 1637551) | | b1553 | orf, hypothetical protein |
| MDS08 | CDS | complement(1637548 . . . 1638081) | | b1554 | |
| MDS08 | CDS | complement(1638078 . . . 1638389) | | b1555 | orf, hypothetical protein |
| MDS08 | CDS | complement(1638394 . . . 1638684) | | b1556 | |
| MDS08 | CDS | complement(1639363 . . . 1639578) | cspB | b1557 | |
| MDS08 | CDS | 1639879 . . . 1640091 | cspF | b1558 | |
| MDS08 | CDS | complement(1640513 . . . 1641295) | | b1559 | |
| MDS08 | CDS | complement(1641279 . . . 1642367) | | b1560 | orf, hypothetical protein |
| MDS08 | CDS | complement(1642675 . . . 1642926) | rem | b1561 | orf, hypothetical protein |
| MDS08 | CDS | complement(1643143 . . . 1643298) | hokD | b1562 | polypeptide destructive to membrane potential |
| MDS08 | CDS | complement(1643370 . . . 1643657) | relE | b1563 | orf, hypothetical protein |
| MDS08 | CDS | complement(1643657 . . . 1643896) | relB | b1564 | negative regulator of translation |
| MDS08 | CDS | 1643921 . . . 1644226 | | b1565 | orf, hypothetical protein |
| MDS08 | CDS | 1644429 . . . 1644761 | flxA | b1566 | orf, hypothetical protein |
| MDS08 | CDS | complement(1645198 . . . 1645347) | | b1567 | orf, hypothetical protein |
| MDS08 | CDS | complement(1645370 . . . 1645660) | | b1568 | orf, hypothetical protein |
| MDS08 | CDS | complement(1645644 . . . 1645874) | dicC | b1569 | regulator of dicB |
| MDS08 | CDS | 1645958 . . . 1646365 | dicA | b1570 | regulator of dicB |
| MDS08 | CDS | 1646532 . . . 1646687 | ydfA | b1571 | orf, hypothetical protein |
| MDS08 | CDS | 1646647 . . . 1646817 | ydfB | b1572 | orf, hypothetical protein |
| MDS08 | CDS | 1646847 . . . 1647065 | ydfC | b1573 | orf, hypothetical protein |
| MDS08 | misc_RNA | 1647406 . . . 1647458 | dicF | b1574 | DicF antisense RNA, inhibits ftsZ translation |
| MDS08 | CDS | 1647633 . . . 1647821 | dicB | b1575 | inhibition of cell division |
| MDS08 | CDS | 1647818 . . . 1648009 | ydfD | b1576 | orf, hypothetical protein |
| MDS08 | CDS | 1648102 . . . 1649022 | ydfE | b1577 | orf, hypothetical protein |
| MDS08 | CDS | 1648905 . . . 1649561 | | b1578 | orf, hypothetical protein |
| MDS08 | CDS | 1649536 . . . 1650732 | | b1579 | |
| MDS09 | CDS | complement(4493213 . . . 4494274) | yjgB | b4269 | putative oxidoreductase |
| MDS09 | tRNA | 4494428 . . . 4494512 | leuX | b4270 | tRNA-Leu |
| MDS09 | CDS | 4494773 . . . 4495963 | intB | b4271 | prophage P4 integrase |
| MDS09 | CDS | 4496250 . . . 4496660 | yi21_6 | b4272 | IS2 hypothetical protein |
| MDS09 | CDS | 4496618 . . . 4497523 | yi22_6 | b4273 | IS2 hypothetical protein |
| MDS09 | CDS | 4497622 . . . 4497957 | yjgW | b4274 | orf, hypothetical protein |
| MDS09 | CDS | complement(4498066 . . . 4498512) | yjgX | b4275 | orf, hypothetical protein |
| MDS09 | CDS | complement(4498455 . . . 4498904) | yjgY | b4276 | orf, hypothetical protein |
| MDS09 | CDS | 4499283 . . . 4499612 | yjgZ | b4277 | orf, hypothetical protein |
| MDS09 | CDS | complement(4500126 . . . 4501454) | yi41 | b4278 | IS4 hypothetical protein |
| MDS09 | CDS | 4502021 . . . 4503298 | yjhB | b4279 | putative transport protein |
| MDS09 | CDS | 4503295 . . . 4504428 | yjhC | b4280 | putative dehydrogenase |
| MDS09 | CDS | complement(4504649 . . . 4505023) | yjhD | b4281 | orf, hypothetical protein |
| MDS09 | CDS | 4504929 . . . 4505132 | yjhE | b4282 | orf, hypothetical protein |
| MDS09 | CDS | 4505184 . . . 4505486 | yi91b | b4283 | |
| MDS09 | CDS | complement(4505489 . . . 4506640) | tra8_3 | b4284 | IS30 transposase |
| MDS09 | CDS | 4506981 . . . 4507577 | | b4285 | putative transposase |
| MDS09 | CDS | 4507743 . . . 4508156 | | b4286 | orf, hypothetical protein |
| MDS09 | CDS | complement(4508713 . . . 4509480) | fecE | b4287 | ATP-binding component of citrate-dependent |
| MDS09 | CDS | complement(4509481 . . . 4510437) | fecD | b4288 | citrate-dependent iron transport, membrane-bound protein |
| MDS09 | CDS | complement(4510434 . . . 4511432) | fecC | b4289 | citrate-dependent iron(III) transport protein, cytosolic |
| MDS09 | CDS | complement(4511429 . . . 4512337) | fecB | b4290 | citrate-dependent iron transport, periplasmic protein |
| MDS09 | CDS | complement(4512376 . . . 4514700) | fecA | b4291 | outer membrane receptor; citrate-dependent iron |
| MDS09 | CDS | complement(4514787 . . . 4515740) | fecR | b4292 | outer membrane receptor; citrate-dependent iron transport, outer membrane receptor |
| MDS09 | CDS | complement(4515737 . . . 4516258) | fecI | b4293 | probable RNA polymerase sigma factor |
| MDS09 | CDS | 4516550 . . . 4516825 | insA_7 | b4294 | IS1 protein InsA |
| MDS09 | CDS | complement(4517361 . . . 4518161) | yjhU | b4295 | orf, hypothetical protein |
| MDS09 | CDS | complement(4518694 . . . 4520043) | yihF | b4296 | putative transport system permease |
| MDS09 | CDS | complement(4520150 . . . 4522117) | yjhG | b4297 | putative dehydratase |
| MDS09 | CDS | complement(4522128 . . . 4523087) | yjhH | b4298 | putative lyase/synthase |
| MDS09 | CDS | complement(4523038 . . . 4523826) | yjhI | b4299 | putative regulator |
| MDS09 | CDS | complement(4524129 . . . 4524911) | sgcR | b4300 | putative DEOR-type transcriptional regulator |
| MDS09 | CDS | complement(4524928 . . . 4525560) | sgcE | b4301 | putative epimerase |
| MDS09 | CDS | complement(4525572 . . . 4526003) | sgcA | b4302 | putative PTS system enzyme II A component |

TABLE 2-continued

| Strain | Type | Coordinates | Name | B | Function |
|---|---|---|---|---|---|
| MDS09 | CDS | complement(4526134 . . . 4526940) | sgcQ | b4303 | putative nucleoside triphosphatase |
| MDS09 | CDS | complement(4526953 . . . 4528266) | sgcC | b4304 | putative PTS system enzyme IIC component |
| MDS09 | CDS | complement(4528553 . . . 4529704) | sgcX | b4305 | putative lyase/synthase |
| MDS09 | CDS | complement(4530460 . . . 4531206) | yjhP | b4306 | putative methyltransferase |
| MDS09 | CDS | complement(4531262 . . . 4531807) | yjhQ | b4307 | orf, hypothetical protein |
| MDS09 | CDS | 4533038 . . . 4534054 | yjhR | b4308 | putative frameshift suppressor" |
| MDS09 | CDS | complement(4534637 . . . 4535617) | yjhS | b4309 | orf, hypothetical protein |
| MDS09 | CDS | complement(4535682 . . . 4536896) | yjhT | b4310 | orf, hypothetical protein |
| MDS09 | CDS | complement(4536808 . . . 4537533) | yjhA | b4311 | orf, hypothetical protein |
| MDS09 | CDS | 4538980 . . . 4539582 | fimB | b4312 | recombinase involved in phase variation; regulator for fimA" |
| MDS09 | CDS | 4540060 . . . 4540656 | fimE | b4313 | recombinase involved in phase variation; regulator for fimA" |
| MDS09 | CDS | 4541138 . . . 4541686 | fimA | b4314 | major type 1 subunit fimbrin (pilin) |
| MDS09 | CDS | 4541643 . . . 4542290 | fimI | b4315 | fimbrial protein |
| MDS09 | CDS | 4542327 . . . 4543052 | fimC | b4316 | periplasmic chaperone, required for type 1 fimbriae |
| MDS09 | CDS | 4543119 . . . 4545755 | fimD | b4317 | outer membrane protein; export and assembly of type 1 fimbriae, interrupted |
| MDS09 | CDS | 4545765 . . . 4546295 | fimF | b4318 | fimbrial morphology |
| MDS09 | CDS | 4546308 . . . 4546811 | fimG | b4319 | fimbrial morphology |
| MDS09 | CDS | 4546831 . . . 4547733 | fimH | b4320 | minor fimbrial subunit, D-mannose specific adhesin |
| MDS10 | CDS | complement(3108612 . . . 3109148) | yghD | b2968 | putative secretion pathway protein |
| MDS10 | CDS | complement(3109150 . . . 3110010) | yghE | b2969 | putative general secretion pathway for protein export (GSP) |
| MDS10 | CDS | complement(3110076 . . . 3110942) | | b2970 | putative general secretion pathway for protein export (GSP) |
| MDS10 | CDS | complement(3111089 . . . 3111499) | | b2971 | orf, hypothetical protein |
| MDS10 | CDS | complement(3111565 . . . 3112497) | | b2972 | |
| MDS10 | CDS | complement(3117619 . . . 3119301) | yghK | b2975 | putative permease |
| MDS10 | CDS | complement(3119656 . . . 3121827) | glcB | b2976 | malate synthase G |
| MDS10 | CDS | complement(3121849 . . . 3122253) | glcG | b2977 | orf, hypothetical protein |
| MDS10 | CDS | complement(3124544 . . . 3126043) | glcD | b2979 | glycolate oxidase subunit D |
| MDS10 | CDS | 3126294 . . . 3127058 | glcC | b2980 | transcriptional activator for glc operon |
| MDS10 | CDS | complement(3127065 . . . 3128237) | | b2981 | orf, hypothetical protein |
| MDS10 | CDS | 3128200 . . . 3129216 | trs5_9 | b2982 | IS5 transposase |
| MDS10 | CDS | complement(3129363 . . . 3130430) | yghQ | b2983 | orf, hypothetical protein |
| MDS10 | CDS | complement(3130476 . . . 3131234) | yghR | b2984 | orf, hypothetical protein |
| MDS10 | CDS | complement(3131266 . . . 3131979) | yghS | b2985 | orf, hypothetical protein |
| MDS10 | CDS | 3132153 . . . 3132845 | yghT | b2986 | orf, hypothetical protein |
| MDS10 | CDS | complement(3132894 . . . 3134393) | pitB | b2987 | low-affinity phosphate transport |
| MDS10 | CDS | complement(3112572 . . . 3117134) | yghJ | b4466 | putative lipoprotein |
| MDS10 | CDS | complement(3122258 . . . 3123481) | glcF | b4467 | glycolate oxidase iron-sulfur subunit |
| MDS10 | CDS | complement(3123492 . . . 3124544) | glcE | b4468 | glycolate oxidase iron-sulfur subunit |
| MDS11 | CDS | complement(1196090 . . . 1196755) | ymfD | b1137 | orf, hypothetical protein |
| MDS11 | CDS | complement(1196756 . . . 1197460) | ymfE | b1138 | orf, hypothetical protein |
| MDS11 | CDS | 1197918 . . . 1198811 | lit | b1139 | phage T4 late gene expression; at locus of e14 element |
| MDS11 | CDS | complement(1198902 . . . 1200029) | intE | b1140 | prophage e14 integrase |
| MDS11 | CDS | complement(1200010 . . . 1200255) | | b1141 | |
| MDS11 | CDS | complement(1200292 . . . 1200603) | ymfH | b1142 | |
| MDS11 | CDS | 1200675 . . . 1201061 | ymfI | b1143 | |
| MDS11 | CDS | complement(1200999 . . . 1201283) | ymfJ | b1144 | |
| MDS11 | CDS | complement(1201482 . . . 1202156) | | b1145 | |
| MDS11 | CDS | 1201944 . . . 1202447 | | b1146 | |
| MDS11 | CDS | 1202479 . . . 1203048 | ymfL | b1147 | |
| MDS11 | CDS | 1203045 . . . 1203383 | ymfM | b1148 | |
| MDS11 | CDS | 1203393 . . . 1204760 | ymfN | b1149 | |
| MDS11 | CDS | 1204772 . . . 1204954 | ymfR | b1150 | |
| MDS11 | CDS | 1204954 . . . 1205427 | ymfO | b1151 | |
| MDS11 | CDS | 1205354 . . . 1206145 | | b1152 | |
| MDS11 | CDS | 1206136 . . . 1206720 | | b1153 | |
| MDS11 | CDS | 1206724 . . . 1207353 | ycfK | b1154 | |
| MDS11 | CDS | 1207355 . . . 1207768 | | b1155 | |
| MDS11 | CDS | complement(1207740 . . . 1208342) | ycfA | b1156 | |
| MDS11 | CDS | complement(1208342 . . . 1208881) | | b1157 | |
| MDS11 | CDS | 1208908 . . . 1209462 | pin | b1158 | inversion of adjacent DNA; at locus of e14 element |
| MDS11 | CDS | 1209569 . . . 1210402 | mcrA | b1159 | restriction of DNA at 5-methylcytosine residues; at locus of e14 element |
| MDS11 | CDS | complement(1210903 . . . 1211226) | ycgW | b1160 | orf, hypothetical protein |
| MDS11 | CDS | complement(1211926 . . . 1212330) | ycgX | b1161 | orf, hypothetical protein |
| MDS11 | CDS | complement(1212551 . . . 1213282) | ycgE | b1162 | putative transcriptional regulator |
| MDS11 | CDS | complement(1213487 . . . 1214698) | | b1163 | orf, hypothetical protein |
| MDS11 | CDS | 1215012 . . . 1215248 | ycgZ | b1164 | orf, hypothetical protein |
| MDS11 | CDS | 1215291 . . . 1215563 | ymgA | b1165 | orf, hypothetical protein |

TABLE 2-continued

| Strain | Type | Coordinates | Name | B | Function |
|---|---|---|---|---|---|
| MDS11 | CDS | 1215592 . . . 1215858 | ymgB | b1166 | orf, hypothetical protein |
| MDS11 | CDS | 1215971 . . . 1216219 | ymgC | b1167 | orf, hypothetical protein |
| MDS11 | CDS | 1216509 . . . 1218074 | | b1168 | putative proteases |
| MDS11 | CDS | 1218824 . . . 1220344 | | b1169 | putative ATP-binding component of a transport system |
| MDS11 | CDS | 1220429 . . . 1221445 | | b1170 | |
| MDS11 | CDS | complement(1221528 . . . 1221863) | | b1171 | orf, hypothetical protein |
| MDS11 | CDS | complement(1221867 . . . 1222151) | | b1172 | orf, hypothetical protein |
| MDS12 | CDS | complement(564038 . . . 565201) | intD | b0537 | prophage DLP12 integrase |
| MDS12 | CDS | 565195 . . . 565755 | | b0538 | putative sensory transduction regulator |
| MDS12 | CDS | complement(565321 . . . 565584) | | b0539 | |
| MDS12 | CDS | 566056 . . . 566364 | | b0540 | |
| MDS12 | CDS | 566361 . . . 567227 | tra5_2 | b0541 | |
| MDS12 | CDS | 567333 . . . 567470 | | b0542 | orf, hypothetical protein |
| MDS12 | CDS | 567538 . . . 567870 | emrE | b0543 | methylviologen resistance |
| MDS12 | CDS | 568125 . . . 569651 | ybcK | b0544 | orf, hypothetical protein |
| MDS12 | CDS | 570116 . . . 570667 | ybcL | b0545 | orf, hypothetical protein |
| MDS12 | CDS | 570677 . . . 571474 | ybcM | b0546 | putative ARAC-type regulatory protein |
| MDS12 | CDS | 571689 . . . 572144 | ybcN | b0547 | orf, hypothetical protein |
| MDS12 | CDS | 572144 . . . 572314 | ninE | b0548 | similar to phage 82 and lambda proteins |
| MDS12 | CDS | 572307 . . . 572597 | ybcO | b0549 | orf, hypothetical protein |
| MDS12 | CDS | 572594 . . . 572956 | rus | b0550 | endodeoxyribonuclease RUS (Holliday junction resolvase) |
| MDS12 | CDS | 573179 . . . 573562 | ybcQ | b0551 | orf, hypothetical protein |
| MDS12 | CDS | complement(573960 . . . 574976) | trs5_2 | b0552 | IS5 transposase |
| MDS12 | CDS | complement(574981 . . . 576108) | nmpC | b0553 | outer membrane porin protein; locus of qsr prophage |
| MDS12 | CDS | 576621 . . . 576836 | ybcR | b0554 | orf, hypothetical protein |
| MDS12 | CDS | 576836 . . . 577333 | ybcS | b0555 | bacteriophage lambda lysozyme homolog |
| MDS12 | CDS | 577330 . . . 577791 | ybcT | b0556 | bacteriophage lambda endopeptidase homolog |
| MDS12 | CDS | complement(577823 . . . 578116) | ybcU | b0557 | bacteriophage lambda Bor protein homolog |
| MDS12 | CDS | complement(578407 . . . 578859) | ybcV | b0558 | putative an envelop protein |
| MDS12 | CDS | 579103 . . . 579309 | ybcW | b0559 | orf, hypothetical protein |
| MDS12 | CDS | 580057 . . . 580602 | nohB | b0560 | bacteriophage DNA packaging protein |
| MDS12 | CDS | 580577 . . . 581320 | ybcX | b0561 | orf, hypothetical protein |
| MDS12 | CDS | complement(581375 . . . 581959) | ybcY | b0562 | orf, hypothetical protein |
| MDS12 | CDS | 582098 . . . 582283 | ylcE | b0563 | orf, hypothetical protein |
| MDS12 | CDS | 582904 . . . 583653 | appY | b0564 | regulatory protein affecting appA and other genes |
| MDS12 | CDS | complement(583903 . . . 584856) | ompT | b0565 | outer membrane protein 3b (a), protease VII |
| MDS13 | CDS | 15445 . . . 16557 | yi81_ | b0016 | IS186 hypothetical protein 1 |
| MDS13 | CDS | complement(15869 . . . 16177) | yi82_1 | b0017 | |
| MDS13 | CDS | complement(16751 . . . 16960) | mokC | b0018 | regulatory peptide whose translation enables hokC (gef) expression |
| MDS13 | CDS | 17489 . . . 18655 | nhaA | b0019 | Na+/H antiporter, pH dependent |
| MDS13 | CDS | 18715 . . . 19620 | nhaR | b0020 | transcriptional activator of nhaA |
| MDS13 | CDS | complement(19811 . . . 20314) | insB_1 | b0021 | IS1 protein InsB |
| MDS13 | CDS | complement(20233 . . . 20508) | insA | b0022 | IS1 protein InsA_1 |
| MDS13 | CDS | complement(16751 . . . 16903) | hokC | b4412 | small toxic membrane polypeptide |
| MDS13 | misc_RNA | 16952 . . . 17006 | sokC | b4413 | antisense RNA blocking mokC (orf69) and hokC (gef) translation |
| MDS14 | CDS | complement(602639 . . . 603886) | ybdG | b0577 | putative transport |
| MDS14 | CDS | complement(603994 . . . 604647) | nfnB | b0578 | oxygen-insensitive NAD(P)H nitroreductase |
| MDS14 | CDS | complement(604741 . . . 605109) | ybdF | b0579 | orf, hypothetical protein |
| MDS14 | CDS | complement(605174 . . . 605422) | ybdJ | b0580 | orf, hypothetical protein |
| MDS14 | CDS | complement(605488 . . . 606606) | ybdK | b0581 | orf, hypothetical protein |
| MDS14 | CDS | 607288 . . . 608400 | yi81_2 | b0582 | IS186 hypothetical protein |
| MDS14 | CDS | 607059 . . . 607211 | hokE | b4415 | small toxic membrane polypeptide |
| MDS15 | CDS | 2507652 . . . 2508908 | | b2389 | orf, hypothetical protein |
| MDS15 | CDS | 2509023 . . . 2509349 | ypeC | b2390 | orf, hypothetical protein |
| MDS15 | CDS | complement(2509490 . . . 2510728) | | b2392 | |
| MDS15 | CDS | 2511064 . . . 2512266 | nupC | b2393 | permease of transport system for3 nucleosides |
| MDS15 | CDS | 2512347 . . . 2513465 | yi81_3 | b2394 | |
| MDS15 | CDS | complement(2513665 . . . 2515971) | yfeA | b2395 | orf, hypothetical protein |
| MDS16 | CDS | complement(379293 . . . 380066) | yaiO | b0358 | orf, hypothetical protein |
| MDS16 | CDS | complement(380068 . . . 380511) | | b0359 | putative transferase |
| MDS16 | CDS | 380530 . . . 380940 | yi21_1 | b0360 | IS2 hypothetical protein |
| MDS16 | CDS | 380898 . . . 381803 | yi22_1 | b0361 | IS2 hypothetical protein |
| MDS16 | CDS | complement(381728 . . . 382114) | | b0362 | orf, hypothetical protein |
| MDS16 | CDS | complement(381963 . . . 383159) | yaiP | b0363 | polysaccharide metabolism |
| MDS16 | CDS | complement(383283 . . . 383693) | yaiS | b0364 | orf, hypothetical protein |
| MDS16 | CDS | 384399 . . . 385418 | tauA | b0365 | taurine transport system periplasmic protein |
| MDS16 | CDS | 385431 . . . 386198 | tauB | b0366 | taurine ATP-binding component of a transport system |

TABLE 2-continued

| Strain | Type | Coordinates | Name | B | Function |
|---|---|---|---|---|---|
| MDS16 | CDS | 386195 . . . 387022 | tauC | b0367 | taurine transport system permease protein |
| MDS16 | CDS | 387019 . . . 387870 | tauD | b0368 | taurine dioxygenase, 2-oxoglutarate-dependent |
| MDS17 | CDS | complement(389121 . . . 389390) | | b0370 | orf, hypothetical protein |
| MDS17 | CDS | 389475 . . . 390935 | yaiT | b0371 | orf, hypothetical protein |
| MDS17 | CDS | complement(390963 . . . 391829) | tra5_1 | b0372 | |
| MDS17 | CDS | complement(391826 . . . 392134) | | b0373 | putative flagellin structural protein |
| MDS17 | CDS | 392239 . . . 393642 | yaiU | b0374 | putative flagellin structural protein |
| MDS17 | CDS | 393685 . . . 394353 | yaiV | b0375 | orf, hypothetical protein |
| MDS17 | CDS | complement(394354 . . . 395511) | yaiH | b0376 | |
| MDS17 | CDS | 395863 . . . 397083 | sbmA | b0377 | sensitivity to microcin B17, possibly envelope protein |
| MDS17 | CDS | 397096 . . . 398190 | yaiW | b0378 | orf, hypothetical protein |
| MDS17 | CDS | complement(398249 . . . 398557) | yaiY | b0379 | orf, hypothetical protein |
| MDS17 | CDS | 398685 . . . 399029 | | b0380 | orf, hypothetical protein |
| MDS18 | CDS | complement(2992959 . . . 2993114) | | b2856 | orf, hypothetical protein |
| MDS18 | CDS | complement(2993336 . . . 2993767) | | b2857 | orf, hypothetical protein |
| MDS18 | CDS | complement(2993770 . . . 2993991) | | b2858 | orf, hypothetical protein |
| MDS18 | CDS | complement(2993984 . . . 2994409) | | b2859 | orf, hypothetical protein |
| MDS18 | CDS | complement(2994394 . . . 2995299) | yi22_4 | b2860 | IS2 hypothetical protein |
| MDS18 | CDS | complement(2995257 . . . 2995622) | yi21_4 | b2861 | IS2 hypothetical protein |
| MDS18 | CDS | complement(2995711 . . . 2996010) | | b2862 | orf, hypothetical protein |
| MDS18 | CDS | complement(2996056 . . . 2996892) | | b2863 | orf, hypothetical protein |
| MDS19 | CDS | 3182802 . . . 3183152 | | b3042 | orf, hypothetical protein |
| MDS19 | CDS | 3183436 . . . 3183987 | ygiL | b3043 | putative fimbrial-like protein |
| MDS19 | CDS | 3184209 . . . 3184574 | yi21_5 | b3044 | IS2 hypothetical protein |
| MDS19 | CDS | 3184532 . . . 3185437 | yi22_5 | b3045 | IS2 hypothetical protein |
| MDS19 | CDS | 3185422 . . . 3187887 | yqiG | b3046 | putative membrane protein |
| MDS19 | CDS | 3187894 . . . 3188652 | yqiH | b3047 | putative membrane protein |
| MDS19 | CDS | 3188654 . . . 3189718 | yqiI | b3048 | orf, hypothetical protein |
| MDS20 | CDS | complement(687220 . . . 688236) | trs5_3 | b0656 | IS5 transposase |
| MDS21 | CDS | 1386912 . . . 1387919 | ycjG | b1325 | putative muconate cycloisomerase I (EC 5.5 |
| MDS21 | CDS | complement(1387894 . . . 1388682) | ycjI | b1326 | putative carboxypeptidase |
| MDS21 | CDS | complement(1388957 . . . 1389889) | | b1327 | orf, hypothetical protein |
| MDS21 | CDS | 1390015 . . . 1390914 | ycjZ | b1328 | putative transcriptional regulator LYSR-type |
| MDS21 | CDS | 1391230 . . . 1392864 | | b1329 | |
| MDS21 | CDS | complement(1392915 . . . 1393946) | | b1330 | orf, hypothetical protein |
| MDS21 | CDS | 1394100 . . . 1395116 | trs5_4 | b1331 | IS5 transposase |
| MDS21 | CDS | 1395389 . . . 1395646 | ynaJ | b1332 | orf, hypothetical protein |
| MDS21 | CDS | complement(1395696 . . . 1396646) | ydaA | b1333 | orf, hypothetical protein |
| MDS22 | CDS | complement(2099919 . . . 2100935) | trs5_7 | b2030 | |
| MDS22 | CDS | complement(2100940 . . . 2101413) | yefJ | b2031 | |
| MDS22 | CDS | complement(2101415 . . . 2102533) | wbbK | b2032 | putative glucose transferase |
| MDS22 | CDS | complement(2102518 . . . 2103108) | wbbJ | b2033 | putative O-acetyl transferase |
| MDS22 | CDS | complement(2103089 . . . 2104081) | wbbI | b2034 | putative Galf transferase |
| MDS22 | CDS | complement(2104084 . . . 2105250) | wbbH | b2035 | O-antigen polymerase |
| MDS22 | CDS | complement(2105250 . . . 2106353) | glf | b2036 | UDP-galactopyranose mutase |
| MDS22 | CDS | complement(2106361 . . . 2107608) | rfbX | b2037 | putative O-antigen transporter |
| MDS22 | CDS | complement(2107605 . . . 2108162) | rfbC | b2038 | dTDP-6-deoxy-D-glucose-3,5 epimerase |
| MDS22 | CDS | complement(2108162 . . . 2109043) | rfbA | b2039 | glucose-1-phosphate thymidylyltransferase |
| MDS22 | CDS | complement(2109101 . . . 2110000) | rfbD | b2040 | dTDP-6-deoxy-L-mannose-dehydrogenase |
| MDS22 | CDS | complement(2110000 . . . 2111085) | rfbB | b2041 | dTDP-glucose 4,6 dehydratase |
| MDS22 | CDS | complement(2111458 . . . 2112351) | galF | b2042 | homolog of Salmonella UTP—glucose-1-P uridyltransferase, probably a UDP-gal transferase |
| MDS22 | CDS | complement(2112526 . . . 2113920) | wcaM | b2043 | orf, hypothetical protein |
| MDS22 | CDS | complement(2113931 . . . 2115151) | wcaL | b2044 | putative colanic acid biosynthesis glycosyl transferase |
| MDS22 | CDS | complement(2115148 . . . 2116428) | wcaK | b2045 | putative galactokinase (EC 2.7.1.6 |
| MDS22 | CDS | complement(2116704 . . . 2118182) | wzxC | b2046 | probable export protein |
| MDS22 | CDS | complement(2118184 . . . 2119578) | wcaJ | b2047 | putative colanic acid biosynthsis UDP-glucose lipid carrier transferase |
| MDS22 | CDS | complement(2119633 . . . 2121003) | cpsG | b2048 | phosphomannomutase |
| MDS22 | CDS | complement(2121108 . . . 2122544) | cpsB | b2049 | mannose-1-phosphate guanyltransferase |
| MDS22 | CDS | complement(2122547 . . . 2123770) | wcaI | b2050 | putative colanic biosynthesis glycosyl transferase |
| MDS22 | CDS | complement(2123767 . . . 2124249) | wcaH | b2051 | GDP-mannose mannosyl hydrolase |
| MDS22 | CDS | complement(2124249 . . . 2125214) | wcaG | b2052 | putative nucleotide di-P-sugar epimerase or dehydratase |
| MDS22 | CDS | complement(2125217 . . . 2126338) | gmd | b2053 | GDP-D-mannose dehydratase |
| MDS22 | CDS | complement(2126364 . . . 2126912) | wcaF | b2054 | putative transferase |
| MDS22 | CDS | complement(2126928 . . . 2127674) | wcaE | b2055 | putative colanic acid biosynthesis glycosyl transferase |
| MDS22 | CDS | complement(2127685 . . . 2128902) | wcaD | b2056 | putative colanic acid polymerase |
| MDS22 | CDS | complement(2128877 . . . 2130094) | wcaC | b2057 | putative glycosyl transferase |
| MDS22 | CDS | complement(2130091 . . . 2130579) | wcaB | b2058 | putative transferase |

TABLE 2-continued

| Strain | Type | Coordinates | Name | B | Function |
|---|---|---|---|---|---|
| MDS22 | CDS | complement(2130582 . . . 2131421) | wcaA | b2059 | putative regulator |
| MDS22 | CDS | complement(2131514 . . . 2133712) | | b2060 | |
| MDS22 | CDS | complement(2133679 . . . 2134122) | wzb | b2061 | low molecular weight protein-tyrosine-phosphatase |
| MDS22 | CDS | complement(2134128 . . . 2135267) | wza | b2062 | putative polysaccharide export protein |
| MDS23 | CDS | complement(2284412 . . . 2286922) | yejO | b2190 | putative ATP-binding component of a transport system |
| MDS23 | CDS | 2286927 . . . 2287049 | | b2191 | orf, hypothetical protein |
| MDS23 | CDS | complement(2287087 . . . 2288103) | trs5_8 | b2192 | IS5 transposase |
| MDS24 | CDS | 3360134 . . . 3360808 | yhcA | b3215 | putative chaperone |
| MDS24 | CDS | 3360829 . . . 3363210 | yhcD | b3216 | putative outer membrane protein |
| MDS24 | CDS | 3363207 . . . 3363686 | yhcE | b3217 | orf, hypothetical protein |
| MDS24 | CDS | complement(3363724 . . . 3364740) | trs5_10 | b3218 | IS5 transposase |
| MDS24 | CDS | 3364948 . . . 3365664 | yhcF | b3219 | putative transcriptional regulator |
| MDS25 | CDS | 3649314 . . . 3650096 | yhiS | b3504 | orf, hypothetical protein |
| MDS25 | CDS | complement(3650205 . . . 3651221) | trs5_11 | b3505 | IS5 transposase |
| MDS26 | CDS | complement(1128637 . . . 1129053) | flgN | b1070 | protein of flagellar biosynthesis |
| MDS26 | CDS | complement(1129058 . . . 1129351) | flgM | b1071 | anti-FliA (anti-sigma) factor; also known as RflB protein |
| MDS26 | CDS | complement(1129427 . . . 1130086) | flgA | b1072 | flagellar biosynthesis; assembly of basal-body periplasmic P ring |
| MDS26 | CDS | 1130241 . . . 1130657 | flgB | b1073 | flagellar biosynthesis, cell-proximal portion of basal-body rod |
| MDS26 | CDS | 1130661 . . . 1131065 | flgC | b1074 | flagellar biosynthesis, cell-proximal portion of basal-body rod |
| MDS26 | CDS | 1131077 . . . 1131772 | flgD | b1075 | flagellar biosynthesis, initiation of hook assembly |
| MDS26 | CDS | 1131797 . . . 1133005 | flgE | b1076 | flagellar biosynthesis, hook protein |
| MDS26 | CDS | 1133025 . . . 1133780 | flgF | b1077 | flagellar biosynthesis, cell-proximal portion of basal-body rod |
| MDS26 | CDS | 1133952 . . . 1134734 | flgG | b1078 | flagellar biosynthesis, cell-distal portion of basal-body rod |
| MDS26 | CDS | 1134787 . . . 1135485 | flgH | b1079 | flagellar biosynthesis, basal-body outer-membrane L (lipopolysaccharide layer) ring protein |
| MDS26 | CDS | 1135497 . . . 1136594 | flgI | b1080 | homolog of Salmonella P-ring of flagella basal body |
| MDS26 | CDS | 1136594 . . . 1137535 | flgJ | b1081 | flagellar biosynthesis |
| MDS26 | CDS | 1137601 . . . 1139244 | flgK | b1082 | flagellar biosynthesis, hook-filament junction protein 1 |
| MDS26 | CDS | 1139256 . . . 1140209 | flgL | b1083 | flagellar biosynthesis; hook-filament junction protein |
| MDS27 | CDS | complement(1960604 . . . 1960996) | flhE | b1878 | flagellar protein |
| MDS27 | CDS | complement(1960996 . . . 1963074) | flhA | b1879 | flagellar biosynthesis; possible export of flagellar proteins |
| MDS27 | CDS | complement(1963067 . . . 1964215) | flhB | b1880 | putative part of export apparatus for flagellar proteins |
| MDS27 | CDS | complement(1964417 . . . 1965061) | cheZ | b1881 | chemotactic response; CheY protein phophatase; antagonist of CheY as switch regulator |
| MDS27 | CDS | complement(1965072 . . . 1965461) | cheY | b1882 | chemotaxis regulator transmits chemoreceptor signals to flagelllar motor components |
| MDS27 | CDS | complement(1965476 . . . 1966525) | cheB | b1883 | response regulator for chemotaxis (cheA sensor); protein methylesterase |
| MDS27 | CDS | complement(1966528 . . . 1967388) | cheR | b1884 | response regulator for chemotaxis protein glutamate methyltransferase |
| MDS27 | CDS | complement(1967407 . . . 1969008) | tap | b1885 | methyl-accepting chemotaxis protein IV peptide sensor receptor |
| MDS27 | CDS | complement(1969054 . . . 1970715) | tar | b1886 | methyl-accepting chemotaxis protein II aspartate sensor receptor |
| MDS27 | CDS | complement(1970860 . . . 1971363) | cheW | b1887 | positive regulator of CheA protein activity |
| MDS27 | CDS | complement(1971384 . . . 1973348) | cheA | b1888 | sensory transducer kinase between chemosignal receptors and CheB and CheY |
| MDS27 | CDS | complement(1973353 . . . 1974279) | motB | b1889 | enables flagellar motor rotation linking torque machinery to cell wall |
| MDS27 | CDS | complement(1974276 . . . 1975163) | motA | b1890 | proton conductor component of motor; no effect on switching |
| MDS27 | CDS | complement(1975290 . . . 1975868) | flhC | b1891 | regulator of flagellar biosynthesis acting on class 2 operons; transcription initiation factor |
| MDS27 | CDS | complement(1975871 . . . 1976230) | flhD | b1892 | regulator of flagellar biosynthesis acting on class 2 operons; transcription initiation factor |
| MDS27 | CDS | complement(1976542 . . . 1977045) | insB_5 | b1893 | IS1 protein InsB |
| MDS27 | CDS | complement(1976964 . . . 1977239) | insA_5 | b1894 | IS1 protein InsA |
| MDS28 | CDS | complement(1995086 . . . 1995838) | yecC | b1917 | putative ATP-binding component of a transport system |

TABLE 2-continued

| Strain | Type | Coordinates | Name | B | Function |
|---|---|---|---|---|---|
| MDS28 | CDS | complement(1995835 . . . 1996503) | yecS | b1918 | putative transport system permease protein (former yecC) |
| MDS28 | CDS | complement(1996518 . . . 1997600) | yedO | b1919 | putative 1-aminocyclopropane-1-carboxylate deaminase |
| MDS28 | CDS | complement(1997609 . . . 1998409) | fliY | b1920 | putative periplasmic binding transport protein |
| MDS28 | CDS | complement(1998497 . . . 1999084) | fliZ | b1921 | orf, hypothetical protein |
| MDS28 | CDS | complement(1999094 . . . 1999813) | fliA | b1922 | flagellar biosynthesis; alternative sigma factor 28; regulation of flagellar operons |
| MDS28 | CDS | complement(2000134 . . . 2001630) | fliC | b1923 | flagellar biosynthesis; flagellin filament structural protein |
| MDS28 | CDS | 2001896 . . . 2003302 | fliD | b1924 | flagellar biosynthesis; filament capping protein; enables filament assembly |
| MDS28 | CDS | 2003327 . . . 2003737 | fliS | b1925 | flagellar biosynthesis; repressor of class 3a and 3b operons (RflA activity) |
| MDS28 | CDS | 2003737 . . . 2004102 | fliT | b1926 | flagellar biosynthesis; repressor of class 3a and 3b operons (RflA activity) |
| MDS28 | CDS | 2004180 . . . 2005667 | amyA | b1927 | cytoplasmic alpha-amylase |
| MDS28 | CDS | complement(2005701 . . . 2006114) | yedD | b1928 | orf, hypothetical protein |
| MDS28 | CDS | 2006301 . . . 2007506 | yedE | b1929 | putative transport system permease protein |
| MDS28 | CDS | 2007503 . . . 2007736 | yedF | b1930 | orf, hypothetical protein |
| MDS28 | CDS | 2007845 . . . 2008513 | yedK | b1931 | orf, hypothetical protein |
| MDS28 | CDS | 2008624 . . . 2009103 | yedL | b1932 | orf, hypothetical protein |
| MDS28 | CDS | complement(2009372 . . . 2009563) | | b1933 | orf, hypothetical protein |
| MDS28 | CDS | complement(2009573 . . . 2009893) | yedN | b1934 | orf, hypothetical protein |
| MDS28 | CDS | complement(2010025 . . . 2010375) | yedM | b1935 | orf, hypothetical protein |
| MDS28 | CDS | 2010526 . . . 2010804 | | b1936 | orf, hypothetical protein |
| MDS28 | CDS | complement(2010724 . . . 2011038) | fliE | b1937 | flagellar biosynthesis; basal-body component, possibly at (MS-ring)-rod junction |
| MDS28 | CDS | 2011253 . . . 2012911 | fliF | b1938 | flagellar biosynthesis; basal-body MS(membrane and supramembrane)-ring and collar protein |
| MDS28 | CDS | 2012904 . . . 2013899 | fliG | b1939 | flagellar biosynthesis, component of motor switching and energizing, enabling rotation and determinin its direction |
| MDS28 | CDS | 2013871 . . . 2014578 | fliH | b1940 | flagellar biosynthesis; export of flagellar proteins |
| MDS28 | CDS | 2014578 . . . 2015951 | fliI | b1941 | flagellum-specific ATP synthase |
| MDS28 | CDS | 2015970 . . . 2016413 | fliJ | b1942 | flagellar fliJ protein |
| MDS28 | CDS | 2016410 . . . 2017537 | fliK | b1943 | flagellar hook-length control protein |
| MDS28 | CDS | 2017642 . . . 2018106 | fliL | b1944 | flagellar biosynthesis |
| MDS28 | CDS | 2018111 . . . 2019115 | fliM | b1945 | flagellar biosynthesis, component of motor switch and energizing, enabling rotation and determining its direction |
| MDS28 | CDS | 2019112 . . . 2019525 | fliN | b1946 | flagellar biosynthesis, component of motor switch and energizing, enabling rotation and determining its direction |
| MDS28 | CDS | 2019588 . . . 2019893 | fliO | b1947 | flagellar biosynthesis |
| MDS28 | CDS | 2019893 . . . 2020630 | fliP | b1948 | flagellar biosynthesis |
| MDS28 | CDS | 2020640 . . . 2020909 | fliQ | b1949 | flagellar biosynthesis |
| MDS28 | CDS | 2020917 . . . 2021702 | fliR | b1950 | flagellar biosynthesis |
| MDS29 | CDS | 4552599 . . . 4553372 | uxuR | b4324 | regulator for uxu operon |
| MDS29 | CDS | complement(4553513 . . . 4554343) | yjiC | b4325 | orf, hypothetical protein |
| MDS29 | CDS | 4555007 . . . 4555408 | yjiD | b4326 | orf, hypothetical protein |
| MDS29 | CDS | complement(4555401 . . . 4556312) | yjiE | b4327 | putative transcriptional regulator LYSR-type |
| MDS29 | CDS | complement(4556377 . . . 4557549) | iadA | b4328 | isoaspartyl dipeptidase |
| MDS29 | CDS | complement(4557562 . . . 4558023) | yjiG | b4329 | orf, hypothetical protein |
| MDS29 | CDS | complement(4558020 . . . 4558715) | yjiH | b4330 | orf, hypothetical protein |
| MDS29 | CDS | 4558851 . . . 4559507 | yjiI | b4331 | orf, hypothetical protein |
| MDS29 | CDS | complement(4559520 . . . 4560698) | yjiJ | b4332 | putative transport protein |
| MDS29 | CDS | complement(4560766 . . . 4561737) | yjiK | b4333 | orf, hypothetical protein |
| MDS29 | CDS | complement(4561945 . . . 4562718) | yjiL | b4334 | putative enzyme |
| MDS29 | CDS | complement(4562722 . . . 4563894) | yjiM | b4335 | orf, hypothetical protein |
| MDS29 | CDS | complement(4563989 . . . 4565269) | yjiN | b4336 | orf, hypothetical protein |
| MDS29 | CDS | complement(4565310 . . . 4566542) | yjiO | p4337 | putative transport protein |
| MDS29 | CDS | 4567021 . . . 4567332 | yjiP | b4338 | orf, hypothetical protein |
| MDS29 | CDS | 4567381 . . . 4567941 | yjiQ | b4339 | orf, hypothetical protein |
| MDS29 | CDS | complement(4568185 . . . 4569597) | yjiR | b4340 | putative regulator |
| MDS29 | CDS | 4569774 . . . 4569938 | yjiS | b4341 | orf, hypothetical protein |
| MDS29 | CDS | 4570389 . . . 4571954 | yjiT | b4342 | orf, hypothetical protein |
| MDS29 | CDS | complement(4574935 . . . 4575981) | mcrC | b4345 | component of McrBC 5-methylcytosine restriction system |
| MDS29 | CDS | complement(4575981 . . . 4577378) | mcrB | b4346 | component of McrBC 5-methylcytosine restriction system |
| MDS29 | CDS | complement(4577522 . . . 4577920) | yjiW | b4347 | orf, hypothetical protein |
| MDS29 | CDS | complement(4578091 . . . 4579485) | hsdS | b4348 | specificity determinant for hsdM and hsdR |
| MDS29 | CDS | complement(4579482 . . . 4581071) | hsdM | b4349 | host modification; DNA methylase M |

TABLE 2-continued

| Strain | Type | Coordinates | Name | B | Function |
|---|---|---|---|---|---|
| MDS29 | CDS | complement(4581272 . . . 4584838) | hsdR | b4350 | host restriction; endonuclease R |
| MDS29 | CDS | 4584972 . . . 4585886 | mrr | b4351 | restriction of methylated adenine |
| MDS29 | CDS | complement(4585932 . . . 4586786) | yjiA | b4352 | orf, hypothetical protein |
| MDS29 | CDS | complement(4586899 . . . 4587102) | yjiX | b4353 | orf, hypothetical protein |
| MDS29 | CDS | complement(4587152 . . . 4589317) | yjiY | b4354 | putative carbon starvation protein |
| MDS29 | CDS | 4589680 . . . 4591335 | tsr | b4355 | methyl-accepting chemotaxis protein I serine sensor receptor |
| MDS29 | CDS | complement(4591384 . . . 4592745) | yjiZ | b4356 | putative transport protein, cryptic orf, joins former yjiZ and yjjL |
| MDS29 | CDS | complement(4592960 . . . 4593874) | yjjM | b4357 | orf, hypothetical protein |
| MDS29 | CDS | 4593998 . . . 4595035 | yjjN | b4358 | putative oxidoreductase |
| MDS29 | CDS | 4572158 . . . 4574878 | yjiV | b4486 | conserved hypothetical protein |
| MDS30 | CDS | 522485 . . . 526765 | rhsD | b0497 | rhsD protein in rhs element |
| MDS30 | CDS | 526805 . . . 527173 | | b0498 | orf, hypothetical protein |
| MDS30 | CDS | 527173 . . . 527883 | | b0499 | orf, hypothetical protein |
| MDS30 | CDS | 527864 . . . 528124 | ybbD | b0500 | orf, hypothetical protein |
| MDS30 | CDS | 528163 . . . 528354 | | b0501 | orf, hypothetical protein |
| MDS30 | CDS | complement(528869 . . . 529276) | | b0502 | orf, hypothetical protein |
| MDS31 | CDS | 728806 . . . 732999 | rhsC | b0700 | |
| MDS31 | CDS | 732593 . . . 732814 | | b0701 | |
| MDS31 | CDS | 732999 . . . 733325 | ybfB | b0702 | orf, hypothetical protein |
| MDS31 | CDS | 733443 . . . 734876 | | b0703 | orf, hypothetical protein |
| MDS31 | CDS | 734873 . . . 735442 | ybfC | b0704 | orf, hypothetical protein |
| MDS31 | CDS | 736327 . . . 737184 | ybfL | b0705 | putative receptor protein |
| MDS31 | CDS | 737315 . . . 738076 | ybfD | b0706 | putative DNA ligase |
| MDS32 | CDS | 1525914 . . . 1527962 | rhsE | b1456 | |
| MDS32 | CDS | 1527946 . . . 1528428 | ydcD | b1457 | orf, hypothetical protein |
| MDS32 | CDS | 1528610 . . . 1529356 | | b1458 | orf, hypothetical protein |
| MDS32 | CDS | 1529400 . . . 1529600 | | b1459 | orf, hypothetical protein |
| MDS32 | CDS | 1529840 . . . 1530976 | ydcC | b1460 | H repeat-associated protein (ORF-H) |
| MDS32 | CDS | 1531076 . . . 1531309 | ydcE | b1461 | orf, hypothetical protein |
| MDS32 | CDS | complement(1531306 . . . 1531923) | | b1462 | orf, hypothetical protein |
| MDS33 | CDS | 3616611 . . . 3617012 | yhhG | b3481 | |
| MDS33 | CDS | 3617215 . . . 3621450 | rhsB | b3482 | rhsB protein in rhs element |
| MDS33 | CDS | 3621437 . . . 3621805 | yhhH | b3483 | orf, hypothetical protein |
| MDS33 | CDS | 3622401 . . . 3623537 | yhhI | b3484 | putative receptor |
| MDS34 | CDS | complement(3759370 . . . 3759978) | yibF | b3592 | putative S-transferase |
| MDS34 | CDS | 3760206 . . . 3764339 | rhsA | b3593 | rhsA protein in rhs element |
| MDS34 | CDS | 3764360 . . . 3765202 | yibA | b3594 | orf, hypothetical protein |
| MDS34 | CDS | 3765244 . . . 3765945 | yibJ | b3595 | orf, hypothetical protein |
| MDS34 | CDS | 3766200 . . . 3766661 | yibG | b3596 | orf, hypothetical protein |
| MDS35 | CDS | complement(1041253 . . . 1043433) | yccC | b0981 | orf, hypothetical protein |
| MDS35 | CDS | complement(1043453 . . . 1043911) | yccY | b0982 | yccY putative phosphatase |
| MDS35 | CDS | complement(1043887 . . . 1045026) | yccZ | b0983 | putative function in exopolysaccharide production |
| MDS35 | CDS | complement(1045072 . . . 1047168) | ymcA | b0984 | orf, hypothetical protein |
| MDS35 | CDS | complement(1047168 . . . 1047914) | ymcB | b0985 | orf, hypothetical protein |
| MDS35 | CDS | complement(1047911 . . . 1048555) | ymcC | b0986 | putative regulator |
| MDS35 | CDS | complement(1048662 . . . 1048985) | ymcD | b0987 | orf, hypothetical protein |
| MDS35 | CDS | 1049250 . . . 1049753 | insB_4 | b0988 | IS1 protein InsB |
| MDS36 | CDS | complement(1085329 . . . 1085742) | ycdP | b1021 | orf, hypothetical protein |
| MDS36 | CDS | complement(1085744 . . . 1087069) | ycdQ | b1022 | orf, hypothetical protein |
| MDS36 | CDS | complement(1087062 . . . 1089080) | ycdR | b1023 | orf, hypothetical protein |
| MDS36 | CDS | complement(1089089 . . . 1091512) | ycdS | b1024 | putative outer membrane protein |
| MDS36 | CDS | 1092099 . . . 1093457 | ycdT | b1025 | orf, hypothetical protein |
| MDS36 | CDS | complement(1093498 . . . 1094364) | tra5_3 | b1026 | |
| MDS36 | CDS | complement(1094361 . . . 1094669) | | b1027 | |
| MDS36 | CDS | 1094746 . . . 1095069 | | b1028 | orf, hypothetical protein |
| MDS36 | CDS | 1095066 . . . 1096052 | ycdU | b1029 | orf, hypothetical protein |
| MDS37 | CDS | 2163174 . . . 2163545 | | b2080 | orf, hypothetical protein |
| MDS37 | CDS | 2163692 . . . 2165053 | yegQ | b2081 | orf, hypothetical protein |
| MDS37 | CDS | complement(2165326 . . . 2165544) | ogrK | b2082 | prophage P2 ogr protein |
| MDS37 | CDS | complement(2165626 . . . 2165772) | | b2083 | orf, hypothetical protein |
| MDS37 | CDS | complement(2165759 . . . 2166025) | | b2084 | orf, hypothetical protein |
| MDS37 | CDS | complement(2166013 . . . 2166390) | yegR | b2085 | orf, hypothetical protein |
| MDS37 | CDS | 2166736 . . . 2167635 | | b2086 | orf, hypothetical protein |
| MDS37 | CDS | complement(2167717 . . . 2168163) | gatR_1 | b2087 | split galactitol utilization operon repressor |
| MDS37 | CDS | 2168251 . . . 2168559 | | b2088 | |
| MDS37 | CDS | 2168556 . . . 2169422 | tra5_4 | b2089 | |
| MDS37 | CDS | complement(2169419 . . . 2169757) | gatR_2 | b2090 | |
| MDS37 | CDS | complement(2169857 . . . 2170897) | gatD | b2091 | galactitol-1-phosphate dehydrogenase |
| MDS37 | CDS | complement(2170945 . . . 2172300) | gatC | b2092 | PTS system galactitol-specific enzyme IIC |
| MDS37 | CDS | complement(2172304 . . . 2172588) | gatB | b2093 | galactitol-specific enzyme IIB of phosphotransferase system |
| MDS37 | CDS | complement(2172619 . . . 2173071) | gatA | b2094 | galactitol-specific enzyme IIA of phosphotransferase system |
| MDS37 | CDS | complement(2173081 . . . 2174343) | gatZ | b2095 | putative tagatose 6-phosphate kinase 1 |
| MDS37 | CDS | complement(2174372 . . . 2175232) | gatY | b2096 | tagatose-bisphosphate aldolase 1 |

TABLE 2-continued

| Strain | Type | Coordinates | Name | B | Function |
| --- | --- | --- | --- | --- | --- |
| MDS37 | misc_RNA | 2165136 . . . 2165221 | ryeE | b4438 | |
| MDS38 | CDS | complement(3577791 . . . 3578828) | yhhX | b3440 | putative regulator |
| MDS38 | CDS | 3579161 . . . 3579649 | yhhY | b3441 | orf, hypothetical protein |
| MDS38 | CDS | 3579886 . . . 3581064 | yhhZ | b3442 | orf, hypothetical protein |
| MDS38 | CDS | 3581061 . . . 3581477 | yrhA | b3443 | orf, hypothetical protein |
| MDS38 | CDS | 3581506 . . . 3581781 | insA_6 | b3444 | IS1 protein InsA |
| MDS38 | CDS | 3581700 . . . 3582203 | insB_6 | b3445 | IS1 protein InsB |
| MDS38 | misc_RNA | complement(3578946 . . . 3579039) | ryhB | b4451 | regulatory RNA mediating Fur regulon |
| MDS39 | CDS | 3718072 . . . 3718284 | cspA | b3556 | cold shock protein 7.4, transcriptional activator of hns |
| MDS39 | CDS | 3718703 . . . 3719224 | yi5A | b3557 | IS150 hypothetical protein |
| MDS39 | CDS | 3719221 . . . 3720072 | t150 | b3558 | IS150 putative transposase |
| MDS39 | CDS | complement(3718471 . . . 3718623) | hokA | b4455 | small toxic membrane polypeptide |
| MDS40 | CDS | 1869885 . . . 1871555 | yeaJ | b1786 | orf, hypothetical protein |
| MDS41 | CDS | 167484 . . . 169727 | fhuA | b0150 | outer membrane protein receptor for ferrichrome, colicin M, and phages T1, T5, and phi80 |
| MDS41 | CDS | 169778 . . . 170575 | fhuC | b0151 | ATP-binding component of hydroxymate-dependent iron transport |
| MDS41 | CDS | 170575 . . . 171465 | fhuD | b0152 | hydroxamate-dependent iron uptake cytoplasmic membrane component |
| MDS41 | CDS | 171462 . . . 173444 | fhuB | b0153 | hydroxamate-dependent iron uptake cytoplasmic membrane component |

SEQUENCE LISTING

The patent contains a lengthy "Sequence Listing" section. A copy of the "Sequence Listing" is available in electronic form from the USPTO web site (http://seqdata.uspto.gov/?pageRequest=docDetail&DocID=US08119365B2). An electronic copy of the "Sequence Listing" will also be available from the USPTO upon request and payment of the fee set forth in 37 CFR 1.19(b)(3).

The invention claimed is:

1. A non-naturally occurring *Escherichia coli* bacterium lacking all genomic and non-genomic IS1, IS2, IS3, IS4, IS5, IS10, IS30, IS150, IS186, IS600 and IS911 insertion sequences, wherein the genome of said bacterium is between 4.41 Mb and 2.78 Mb.

2. The bacterium of claim 1, wherein its genome is between 4.27 Mb and 2.78 Mb.

3. The bacterium of claim 1, wherein its genome is between 4.00 Mb and 2.78 Mb.

4. The bacterium of claim 1, wherein its genome is between 3.71 Mb and 2.78 Mb.

5. The bacterium of claim 1, wherein the parent strain of said bacterium is selected from the group consisting of DH10B, DH5α, INVα, Top10, Top10F, JM103, JM105, JM109, MC1061, MC4100, XL1-Blue, EC100, and EC300.

6. The bacterium of claim 1, wherein the bacterium is competent to be transformed.

7. The bacterium of claim 1, wherein the bacterium lacks Insertion Sequence mini-circles.

8. The bacterium of claim 1, wherein the bacterium comprises a vector.

9. The bacterium of claim 8, wherein the vector lacks insertion sequences.

10. The bacterium of claim 9, wherein the vector comprises a nucleic acid encoding a polypeptide, and wherein the nucleic acid is operatively linked to an expression control sequence.

11. The bacterium of claim 9, wherein the vector is a plasmid.

12. A method of propagating a nucleic acid comprising:

(a) transforming a bacterium according to claim 1 with a nucleic acid to create a transformed bacterium; and (b) propagating the transformed bacterium of step (a) under conditions that allow replication of said nucleic acid.

13. The method of claim 12, wherein the bacterium is transformed by electroporation.

14. A method of producing a polypeptide comprising:

(a) incubating a bacterium according to claim 10 under suitable nutrient conditions to allow expression of the polypeptide; and (b) optionally isolating and purifying said polypeptide.

* * * * *

UNITED STATES PATENT AND TRADEMARK OFFICE
CERTIFICATE OF CORRECTION

PATENT NO. : 8,119,365 B2
APPLICATION NO. : 11/400711
DATED : February 21, 2012
INVENTOR(S) : Frederick R. Blattner et al.

It is certified that error appears in the above-identified patent and that said Letters Patent is hereby corrected as shown below:

In the Specification

Column 1, line 17, insert --This invention was made with government support under GM035682 awarded by the National Institutes of Health. The government has certain rights in the invention.--.

Signed and Sealed this
Twenty-fifth Day of November, 2014

Michelle K. Lee
*Deputy Director of the United States Patent and Trademark Office*